US010765314B2

(12) United States Patent
Yam et al.

(10) Patent No.: US 10,765,314 B2
(45) Date of Patent: Sep. 8, 2020

(54) DISPLAY SYSTEM AND METHOD

(71) Applicant: NOVA-SIGHT LTD., Airport (IL)

(72) Inventors: Ran Yam, Airport (IL); Michael Belkin, Airport (IL); Dan Oz, Airport (IL); Oren Yehezkel, Airport (IL)

(73) Assignee: NOVASIGHT LTD., Airport City (IL)

( * ) Notice: Subject to any disclaimer, the term of this patent is extended or adjusted under 35 U.S.C. 154(b) by 127 days.

(21) Appl. No.: 16/098,885

(22) PCT Filed: May 28, 2017

(86) PCT No.: PCT/IL2017/050591
§ 371 (c)(1),
(2) Date: Nov. 5, 2018

(87) PCT Pub. No.: WO2017/208227
PCT Pub. Date: Dec. 7, 2017

(65) Prior Publication Data
US 2019/0200858 A1    Jul. 4, 2019

Related U.S. Application Data

(60) Provisional application No. 62/342,959, filed on May 29, 2016.

(51) Int. Cl.
*A41B 3/12* (2006.01)
*A61B 3/12* (2006.01)
(Continued)

(52) U.S. Cl.
CPC .............. *A61B 3/12* (2013.01); *A61B 3/0041* (2013.01); *A61B 3/032* (2013.01); *A61B 3/113* (2013.01)

(58) Field of Classification Search
CPC ......... A61B 3/14; A61B 3/0008; A61B 3/102; A61B 3/12; A61B 3/13; A61B 3/0041; A61B 3/0058
(Continued)

(56) References Cited

U.S. PATENT DOCUMENTS 5,094,521 A   3/1992  Jolson et al.
5,875,018 A   2/1999  Lamprecht
(Continued)

FOREIGN PATENT DOCUMENTS

CN    201879982 U    6/2011
CN    105069304 A    11/2015
(Continued)

OTHER PUBLICATIONS

International Search Report and Written Opinion for PCT/IL2017/050591, dated Oct. 2, 2017.
(Continued)

*Primary Examiner* — Hung X Dang
(74) *Attorney, Agent, or Firm* — The Law Office of Joseph L. Felber

(57) ABSTRACT

A system for improving a patient's vision, comprising means for diagnosing and monitoring a deterioration in macular vision or macular vision loss in the patient's eye, and means for augmenting the use of a preferred retinal location (PRL) and eccentric fixation in case the deterioration in macular vision or macular vision loss was detected. A method for improving a patient's vision, comprising: diagnosing and monitoring a deterioration in macular vision or macular vision loss in the patient's eye; and augmenting the use of a preferred retinal location (PRL) and eccentric fixation in case the deterioration in macular vision or macular vision loss was detected.

14 Claims, 16 Drawing Sheets

(51) Int. Cl.
*A61B 3/00* (2006.01)
*A61B 3/032* (2006.01)
*A61B 3/113* (2006.01)

(58) Field of Classification Search
USPC ........ 351/211, 210, 209, 246, 221, 206, 205
See application file for complete search history.

(56) References Cited

U.S. PATENT DOCUMENTS

| | | | |
|---|---|---|---|
| 6,099,124 | A | 8/2000 | Hidaji |
| 7,206,022 | B2 | 4/2007 | Miller et al. |
| 7,859,562 | B2 | 12/2010 | Igarashi et al. |
| 8,057,036 | B2 | 11/2011 | Hess et al. |
| 9,844,317 | B2 | 12/2017 | Green |
| 2001/0050754 | A1 | 12/2001 | Hay et al. |
| 2002/0015957 | A1 | 2/2002 | Hageman et al. |
| 2006/0087618 | A1 | 4/2006 | Smart et al. |
| 2006/0256083 | A1 | 11/2006 | Rosenberg |
| 2007/0033543 | A1 | 2/2007 | Ngari et al. |
| 2009/0079937 | A1 | 3/2009 | Chen et al. |
| 2009/0153796 | A1 | 6/2009 | Rabner |
| 2010/0177179 | A1 | 7/2010 | Behm et al. |
| 2011/0043644 | A1 | 2/2011 | Munger et al. |
| 2011/0050546 | A1 | 3/2011 | Swartz et al. |
| 2011/0304821 | A1 | 12/2011 | Tanassi et al. |
| 2012/0269266 | A1 | 10/2012 | Lin et al. |
| 2012/0307203 | A1 | 12/2012 | Vendel et al. |
| 2013/0044291 | A1 | 2/2013 | Kato et al. |
| 2013/0215147 | A1 | 8/2013 | Hikes et al. |
| 2014/0028976 | A1* | 1/2014 | Tanassi .................. A61B 3/12 351/208 |
| 2014/0208263 | A1 | 7/2014 | Maklouf |
| 2015/0110368 | A1 | 4/2015 | Solanki et al. |
| 2015/0223688 | A1 | 8/2015 | Wang et al. |
| 2015/0243036 | A1 | 8/2015 | Hoffmann et al. |
| 2015/0257967 | A1 | 9/2015 | Simmons |
| 2015/0363905 | A1 | 12/2015 | Pepperell et al. |
| 2016/0000317 | A1 | 1/2016 | Krall et al. |
| 2016/0007849 | A1 | 1/2016 | Krueger |
| 2016/0037137 | A1 | 2/2016 | Seiflein |
| 2016/0073869 | A1 | 3/2016 | Bailey |
| 2016/0109652 | A1 | 4/2016 | Schowengerdt |
| 2016/0270656 | A1 | 9/2016 | Samec et al. |
| 2016/0292856 | A1 | 10/2016 | Niemeijer et al. |
| 2018/0168444 | A1 | 6/2018 | Foss |

FOREIGN PATENT DOCUMENTS

| | | |
|---|---|---|
| CN | 105561562 A | 5/2016 |
| EP | 2457498 A1 | 5/2012 |
| EP | 2 621 169 | 7/2013 |
| EP | 2 689 719 | 1/2015 |
| GB | 2 372 683 | 8/2002 |
| JP | 2010-233978 A | 10/2010 |
| KR | 1020110065935 | 1/2013 |
| RU | 2011-101632 A | 7/2012 |
| WO | 1999/26126 A1 | 5/1999 |
| WO | 2003/092482 | 11/2003 |
| WO | 2008/013907 A2 | 1/2008 |
| WO | 2013/035086 | 3/2013 |
| WO | 2015/145111 | 10/2015 |
| WO | 2016/103259 | 6/2016 |
| WO | 2016/139662 | 9/2016 |
| WO | 2017/208227 | 12/2017 |

OTHER PUBLICATIONS

International Preliminary Report on Patentability for PCT/IL2017/050591, dated Dec. 31, 2018.

International Search Report and Written Opinion for PCT/2017/051063, dated Dec. 13, 2017.

Jones et al., Automated Measurement of Resolution Acuity in Infants Using Remote Eye-Tracking, Visual Psychophysics and Physiological Optics, IOVS, vol. 55, No. 12, Dec. 2014, pp. 8102-8110.

Kooiker, M.J., Pel, J.J., van der Steen-Kant, S.P., van der Steen, J. A Method to Quantify Visual Information Processing in Children Using Eye Tracking. J. Vis. Exp. (113), e54031, doi:10.3791/54031 (2016).

* cited by examiner

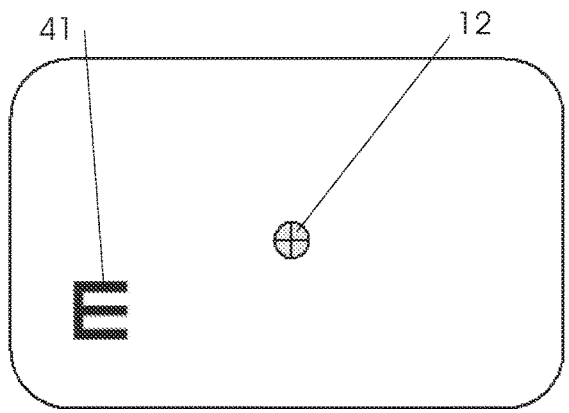
Figure 8A
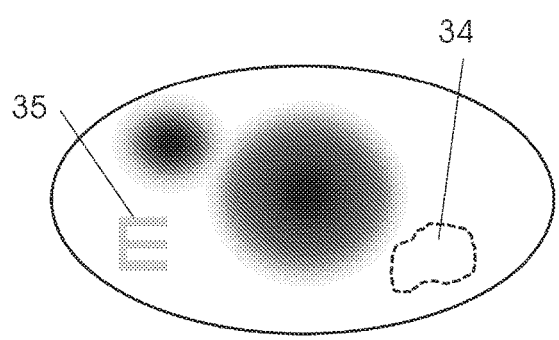
Figure 8B
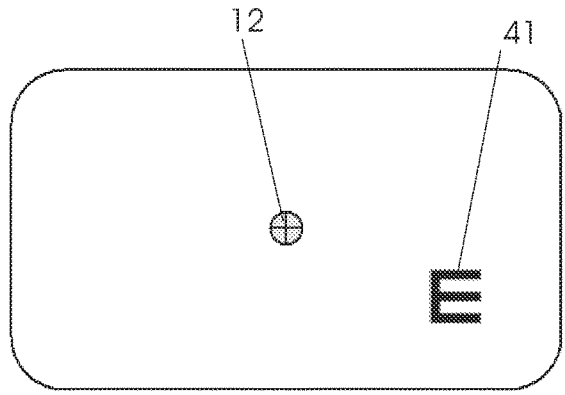
Figure 9A
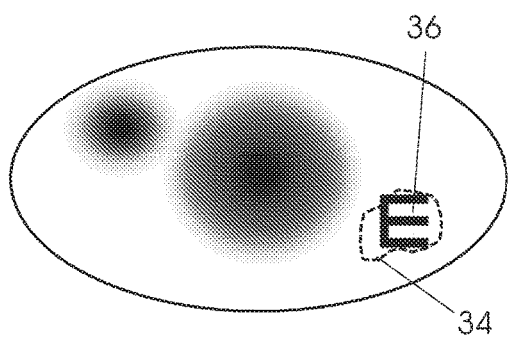
Figure 9B
Figure 10A
Figure 10B
Figure 10C

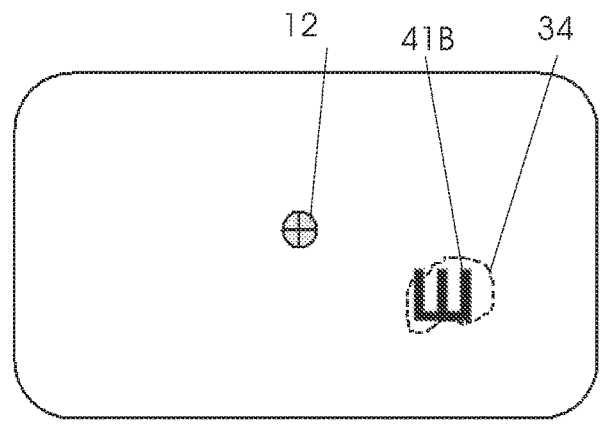
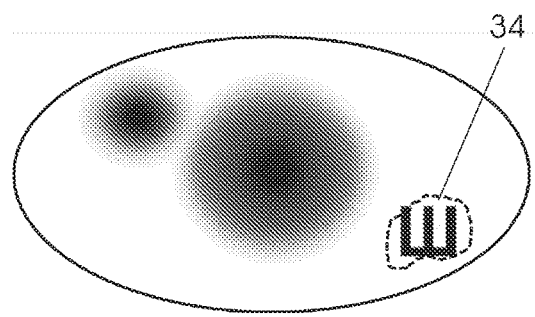
Figure 11A          Figure 11B
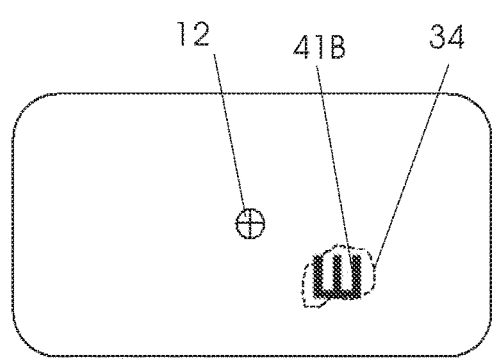
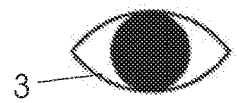
Figure 12A
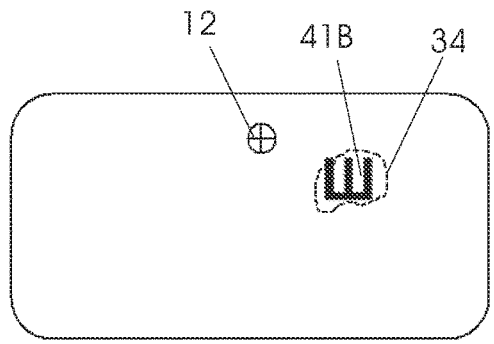
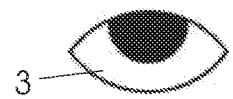
Figure 12B
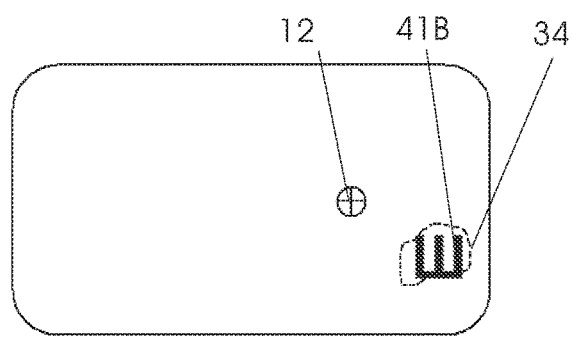
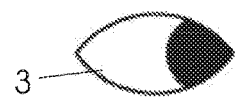
Figure 12C

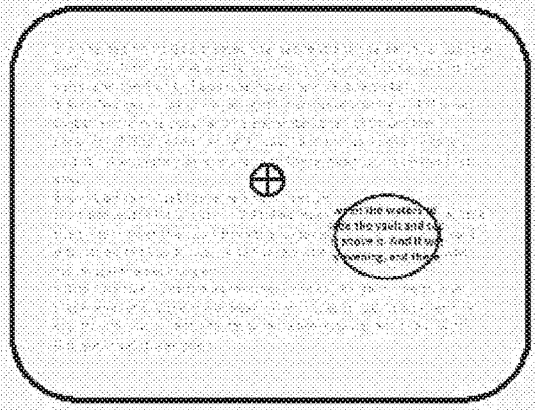
Figure 22A
Figure 22B
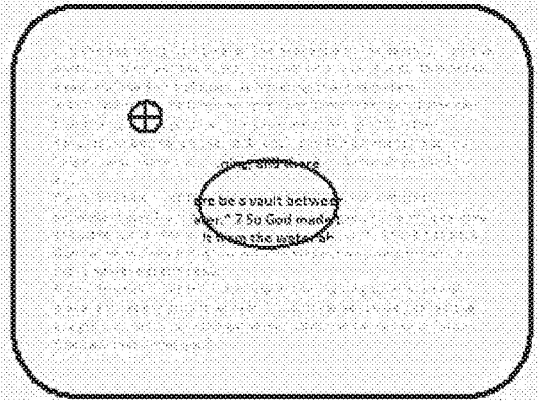
Figure 22C
Figure 22D

DISPLAY SYSTEM AND METHOD

The present application claims priority from Provisional Patent Application No. 62/342,959 filed in the United States on 29 May 2016 by the present inventors.

BACKGROUND

Technical Field

The present invention relates to ophthalmology and more specifically, to systems and methods for diagnosing and monitoring a deterioration in macular vision or macular vision loss, and for augmenting and training the use of a preferred retinal location and eccentric fixation in case a deterioration in macular vision or macular vision loss is detected.

Description of Related Art

The normal retina consists of two main regions (see FIG. 1):
1. The macula: Located near the center of the retina, it covers about 10 to 16 degrees of the central vision 13, or about 5 to 8 degrees each side of the gazing direction 12. The macula has a high concentration of photoreceptors (cones), high visual acuity and color perception, but require more light intensity than the rods in the peripheral region. The high acuity macula region is responsible for the fine image details required for everyday tasks such as reading, concentrating on details, colors discrimination and so on. The center of the macula, where visual perception is at its highest, is called the fovea.
2. Peripheral region: The field of view 11 of this region spreads from the macula to about ±90 to ±100 degrees in both sides, to the limits 16 and 17. It has a relatively low concentration of photoreceptors (rods), poor vision acuity, mostly black and white perception, but a higher sensitivity than the macular area.

If the performance of the macular region deteriorates, for example due to a macular scotoma, a Preferred Retinal Location (PRL) 14 may develop on the peripheral region. Multiple PRLs can be developed and used.

The PRL may replace the function of the macula, to a limited extent, to help the patient see.

A simple pictorial example of normal image perception is depicted in FIGS. 2 and 3. FIG. 2A shows a scene image on a display. The gazing direction 12 is shown in FIGS. 2A and 2C.

In this example, the person is looking at the center of the image. FIG. 2B shows that the central area 312 of the image perceived by the subject is detailed but the peripheral region 311 is blurred. (This is a simplistic illustration; in reality there is a gradual transition between the regions, rather than a sharp border).

In FIG. 3A the person looks at the right side of the image as denotes by gazing direction 12. FIG. 3B shows that now, the detailed region 312 also moved to the right due to the fact that the macular region is stimulated now by that area.

Between 2% and 4% of the total population and up to 60% of the aging population suffer from vision loss not readily correctable with ordinary optical or medical intervention. As life expectancy increases, a growing concern over the quality of life of these people has led to studies aimed at investigating ways of improving their visual performance, but the inability to effectively treat most types of macular degenerations is still high, leading to an increase in the number of low-vision patients. Macular diseases such as AMD, Stargardt, cone-dystrophy, macular myopic degeneration, vitelliform dystrophy and posttraumatic macular scars, are ocular pathologies that affect the central retinal area (macula).

These diseases are leading to a reduction in visual acuity, contrast sensitivity, color perception, ocular motility, reading speed, space perception, fixation stability and/or altered stereopsis, and are accompanied by the appearance of a scotoma (blind area) 32 in the central field causing visual impairment—see for example FIG. 4B. The patient is gazing at the center of the picture, see FIG. 4A. One can see that the blurred peripheral region 311 (FIG. 5B) perception remains similar to a normal eye peripheral region as shown in FIG. 2B.

The degree of visual impairment in such subjects depends on the location of the retinal damage and may vary according to the age of the patients, the presence of other systemic pathologies, the environment in which they live, their education level and/or the psychological response to their condition.

FIG. 5B shows the perception of a person with macular scotoma 32 and a deteriorated peripheral vision 311. FIG. 5A shows the gazing direction 12.

PRL Development, a New Retinal Fixation Zone in Case of Central Vision Loss

When central vision is damaged, most patients automatically adapt to their impairment by using a part of the healthy eccentric parts of the retina for fixation; these eccentric retinal areas are called "Preferred Retinal Loci" (PRLs) 14 (see FIG. 1). The PRL plays the role of a "pseudo-fovea" (see references 1-3 below). It has been shown that occasionally, more than one PRL may occur, especially in patients with long-lasting scotomas, and that the PRL locations can vary with viewing conditions or the duration of disease (see references 4-7).

The visual acuity, color perception and other parameters of the PRL are much worse than of the macula region but it is the only substitute for the patient in order to have some vision at all. The precision and accuracy of eye movements with an eccentric PRL are worse than those with the fovea.

Fixation stability and retinal locations for PRLs are usually not optimal for best visual performance since they are less able to hold a steady fixation (see references 8-12). The normal saccadic eye movements are affected: they become inaccurate, slower, and more frequent, with longer initiation latencies than in normally sighted observers (see references 13-14).

Two important aspects of an eccentric PRL are fixation stability and retinal location.

Fixation stability refers to the precision of eye fixation when one fixates intently on a stimulus for a certain period of time (see reference 15). Fixation stability has traditionally been quantified by calculating the area of an ellipse which encompasses fixation points for a given proportion of eye positions during one fixation trial.

This area is known as the Bivariate Contour Ellipse Area (BCEA) (see reference 16). A smaller BCEA correlates to a more stable fixation whereas, if the eye "wanders", a large BCEA is formed and will be regarded as impaired fixation. Research shows that people with central vision loss have impaired fixation stability and this may contribute to their poor visual performance (see references 17-18).

Recent research shows that the ability to fixate is flexible in patients with a central vision loss; that a new PRL can be trained and fixation stability improved, resulting in better visual performance including better reading performance.

The ability to fixate one's vision, that is to keep a stable gazing direction 12 pointing at a particular object without the eye losing its aim, may seem obvious to people having normal vision; however, for people with impaired vision looking at something through their peripheral region, this may be a difficult task indeed.

VA Changes According to the Retinal Location

In normal eyes, visual acuity drops off rapidly away from the fovea. The macular area immediately surrounding the fovea has an acuity of 6/20. Moving outward from the macula, visual acuity drops to 6/120 and less.

Examples of Existing PRL Training Approaches

1. Visual Awareness and Eccentric Viewing

Awareness of the PRL location and eccentric viewing can be improved by training. The purpose of these training exercises is to allow the subjects to appreciate perceptual alterations that occur when using a PRL and to practice making perceptual discriminations with the peripheral retina. For example, during the exercises a clock face display is presented, with hour markings at its periphery and a star at the center. Subjects are asked to place their fixation along the meridian of each hour location. The clarity of the center star when looking straight at it is compared with its clarity when viewing eccentrically.

For example, if the best vision is in the upper part of the retina, the patient is asked to look up to, cover the 12 o'clock number with his/her scotoma. Thereby, the patient views better the star at the center of the clock face (see references 19-21).

2. Control of Reading Eye Movements

Control of eye movements is trained during a series of saccade tasks. Eye movements are monitored using a camera focused on the pupils of the tested eyes. The experimenter monitors pupil movements, providing feedback to the subjects (see reference 22).

3. Reading Practice with Sequential Presentation of Lexical Information

A number of studies show improvements in reading performance after patients are prescribed a magnifier and provided with practice reading text (see reference 23). The training exercises used in these studies implicitly combined oculomotor, perceptual, attention, and cognitive aspects of reading practice.

References

1. Von Noorden G K, Mackensen G. Phenomenology of eccentric fixation. Am J Ophthalmol. 1962 April; 53:642-660 White & Bedell, 1990;

2. Guez J-E, Gargasson J-FL, Rigaudiere F, O'Regan J K. Is there a systematic location for the pseudo-fovea in patients with central scotoma? Vision Research. 1993;9:1271-1279.

3. Fletcher D C, Schuchard R A. Preferred retinal loci. Relationship to macular scotomas in a low vision population. Ophthalmology. 1997;104:632-638.

4. Lei H, Schuchard R A. Using two preferred retinal loci for different lighting conditions in patients with central scotomas. Investigative Ophthalmology and Visual Science. 1997;38:1812-1818.

5. Duret F, Issenhuth M, Safran A B. Combined use of several preferred retinal loci in patients with macular disorders when reading single words. Vision Research. 1999; 39:873-879.

6. Crossland M D, Culham L E, Kabanarou S A, Rubin G S. Preferred retinal locus development in patients with macular disease. Ophthalmology. 2005;112:1579-1585.

7. Crossland, M. D., Sims, M., Galbraith, R. F. & Rubin, G. S. (2004). Evaluation of a new quantitative technique to assess the number and extent of preferred retinal loci in macular disease. Vision Research 44,1537-1546.

8. Culham, L., Fitzke, F. W., Timberlake, G. T., & Marshall, J. (1993). Assessment of fixation stability in normal subjects and patients using a scanning laser ophthalmoscope. Clinical Vision Sciences, 8, 551-561.

9. Schuchard, R. A., & Raasch, T. W. (1992). Retinal locus for fixation: Pericentral fixation targets. Clinical Vision Sciences, 7, 511-520.

10. Steinman, R. M., Cushman, W. B., & Martins, A. J. (1982). The precision of gaze. A review. Human Neurobiology, 1, 97-109.

11. White, J. M., & Bedell, H. E. (1990). The oculomotor reference in humans with bilateral macular disease. Investigative Ophthalmology and Visual Science, 31, 1149-1161.

12. Whittaker, S. G., Budd, J., & Cummings, R. W. (1988). Eccentric fixation with macular scotoma. Investigative Ophthalmology and Visual Science, 29, 268-278.

13. White, J. M., & Bedell, H. E. (1990). The oculomotor reference in humans with bilateral macular disease. Investigative Ophthalmology and Visual Science, 31, 1149-1161.

14. Whittaker, S. G., Cummings, R. W., & Swieson, L. R. (1991). Saccade control without a fovea. Vision Research, 31, 2209-2218.

15. Gonzalez, E. G., Teichman, J., Markowitz, S. N., Lillakas, L. & Steinbach, M. J. (2006). Fixation stability using radial gratings in patients with age-related macular degeneration. Canadian Journal of Ophthalmology 41,333-339.

16. Steinman, R. M. 1965 Effect of target size, luminance, and color on monocular fixation Journal of the Optical Society of America, 55 (1965), pp. 1158-1165.

17. Timberlake, G. T., Mainster, M. A., Peli, E., Augliere, R. A., Essock, E. A. & Arend, L. E. (1986). Reading with a macular scotoma. I. Retinal location of scotoma and fixation area. Investigative Ophthalmology & Visual Science 7,1137-1147.

18. Timberlake, G. T., Sharma, M. K., Grose, S. A., Gobert, D. V., Gauch, J. M. & Maino, J. H. (2005). Retinal location of the preferred retinal locus relative to the fovea in scanning laser ophthalmoscope images. Optometry & Vision Science 82,177-185.

19. Goodrich G L, Quillman R D. Training eccentric viewing. J Vis Impairment Blindness. 1977;71:377-381.

20. Maplesden C. A subjective approach to eccentric viewing training. J Vis Impairment Blindness. 1984;78:5-6.

21. Quillman R D. Low Vision Training Manual. Kalamazoo, Mich.: Western Michigan University; 1980.22. Whittaker S G, Lovie-Kitchin J. Visual requirements for reading. Optom Vision Sci. 1993;70:54-65.

23. Nilsson U L. Visual rehabilitation with and without educational training in the use of optical aids and residual vision: a prospective study of patients with advanced age-related macular degeneration. Clin Vision Sci. 1990;6:3-10.

Patents and Patent Applications Citations

U.S. 2015110368 (A1)—2015 Apr. 23 SYSTEMS AND METHODS FOR PROCESSING RETINAL IMAGES FOR SCREENING OF DISEASES OR ABNORMALITIES.

WO09926126 (A1)—1999 May 27 USER INTERFACE

CN105069304 (A)—2015 Nov. 18 Machine learning-based method for evaluating and predicting ASD.

CN105561562 (A)—2016 May 11 Visual motion tracking training system and method thereof.

EP2457498 (Al)—2012 May 30 Method and system to monitor retinal ischemia.

RU2011101632 (A)—2012 May 27 METHOD OF TREATING FUNCTIONAL VISUAL DISTURBANCES AND DEVICE FOR ITS REALISATION.

JP2010233978 (A)—2010 Oct. 21 VISUAL PERFORMANCE INSPECTION DEVICE.

CN201879982 (U)—2011 Jun. 29 Treatment device used for sight improving and recovering training.

U.S. 20160292856(A1)—2016 Oct. 6 SYSTEMS AND METHODS FOR FEATURE DETECTION IN RETINAL IMAGES.

These and other problems in prior art methods for diagnosing, monitoring and training in case of a deterioration in macular vision are addressed with the present invention.

SUMMARY OF THE INVENTION

The present invention relates to a system for mapping and training retinal impaired patients to establish, monitor and promote a preferred retinal location (PRL) using eye tracking.

According to a novel feature of the present invention, in a preferred embodiment, the mapping and monitoring of the retinal performance include the following steps: The retina will be tested and mapped. According to the new method, all the area of the retina will be scanned by a focalized stimulus while preventing the rest of the retinal locations from receiving any visual stimuli. This way, the patient visual attention will be concentrated on the stimulus only.

Furthermore, the location of the focalized stimulus is stabilized on the retina with the aid of eye trackers—that is, if the gazing direction changes, the focalized stimulus will move correspondingly, so as to keep the stimulus on the same location on the retina. Otherwise, the stimulus may appear as an indistinct blur and mapping may be hindered or may be impossible to perform. For details see for example FIGS. 16A, 16B and 16C.

The performance of each retinal location will be evaluated and registered. The size, shape and number of the distinct areas can be determined for each subject according to the retinal condition. Each retinal location will be tested for one or more of the following spatial and temporal parameters: visual acuity, reading acuity, reading speed, contrast sensitivity, crowding, reaction time, saccades, fixation stability, size of healthy area, color test, temporal JND (just-noticeable difference), orientation discrimination and/or optical distortions. The information will be recorded.

After attaining retinal mapping, the most suitable retinal locations for PRL can be defined and registered.

The mapping procedure can be repeated periodically in order to monitor the retinal condition—the location, the size and characteristics of this area can be modified according to the individual progress of the disease and the training paradigm. Multiple PRLs can be mapped and used.

The training will be performed (after knowing the location of the best PRL) by obscuring, fully or partially, the whole image on display except for the area associated with that PRL. There are two possible embodiments for the next stage of the method:

a. This specific image will move on the screen as shown in FIGS. 16A, 16B and 16C according to the gazing direction so as to enforce the patient to see only that part of image; or b. The obscuring mask will move on the display and will present on the PRL different parts of the image while obscuring the rest, as shown in New FIG. 22.

Further purposes and benefits of the current invention will become apparent to persons skilled in the art upon reading the present disclosure and the related drawings.

BRIEF DESCRIPTION OF THE DRAWINGS

Embodiments of the invention are disclosed hereinafter with reference to the drawings, in which:

FIG. 8 illustrates a mapping phase, with target at left down side.

FIG. 9 illustrates a mapping phase, with target at right down side.

FIG. 10 illustrates a mapping phase—visual acuity evaluation various targets.

FIG. 11 illustrates a mapping phase—evaluating visual acuity.

FIG. 12 illustrates a mapping phase—constant retinal location on display using eye trackers.

FIG. 22 illustrates a training method using a movable obscuring mask.

DETAILED DESCRIPTION OF THE INVENTION

The current invention will now be described by way of example and with reference to the accompanying drawings.

Figure 1:
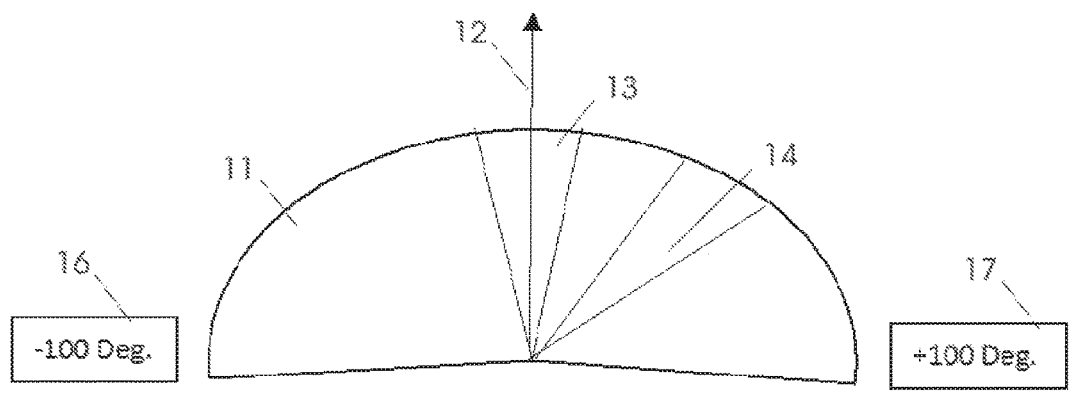
FIG. 1 illustrates a normal eye field of view.
Figure 2A:
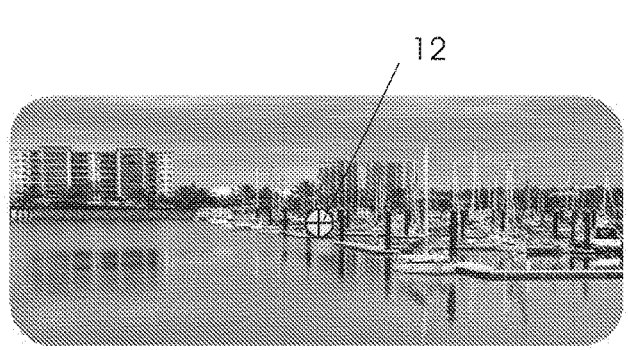
FIG. 2 illustrates a normal eye, straight-on gaze.
Figure 2B:
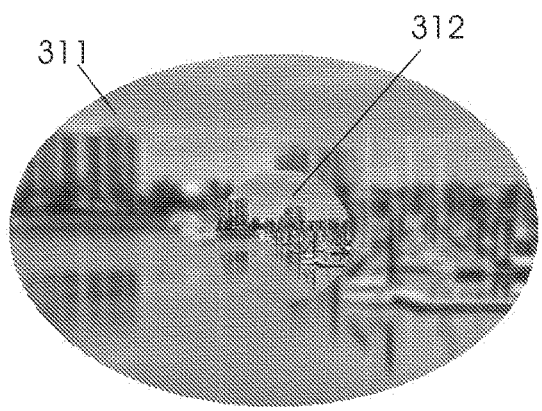
Figure 2C:
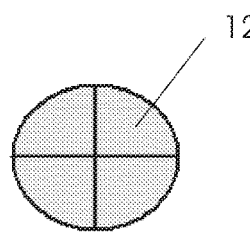
Figure 3A:
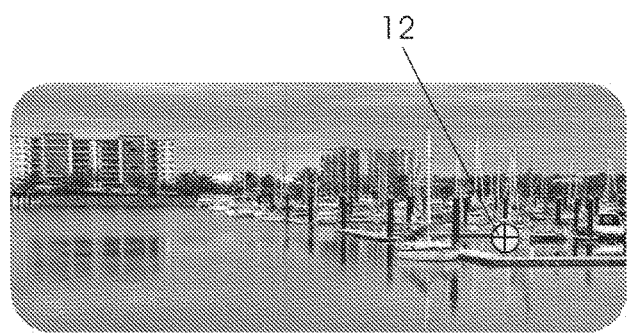
FIG. 3 illustrates a normal eye, right side gaze.
Figure 3B:
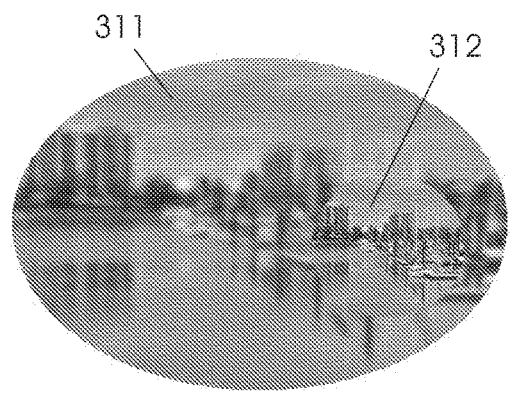
Figure 4A:
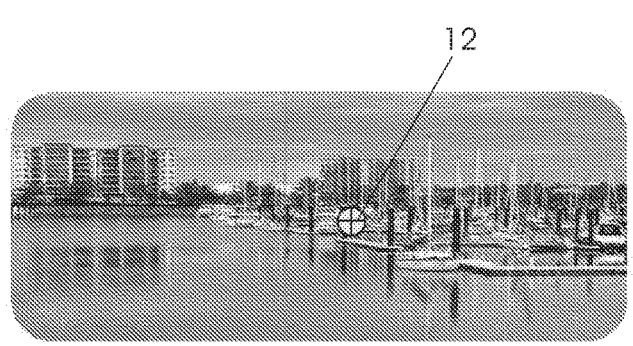
FIG. 4 illustrates a macular scotoma, straight-on gaze.
Figure 4B:
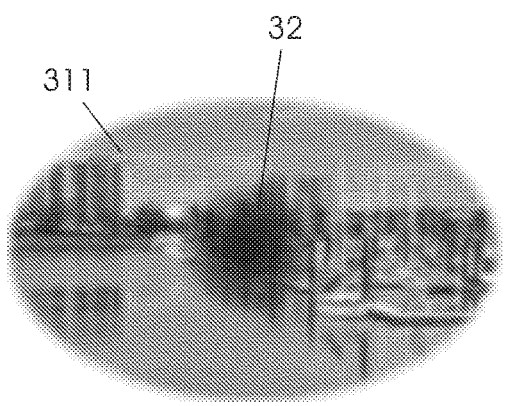
Figure 5A:
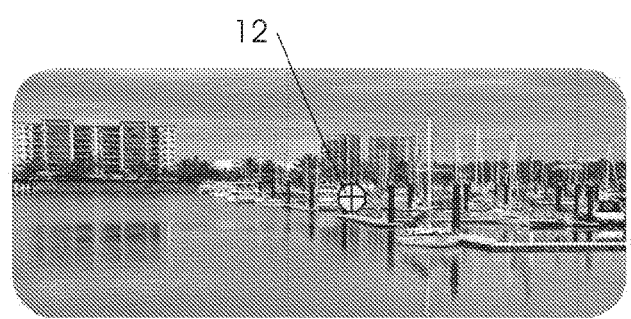
FIG. 5 illustrates a macular scotoma with deteriorated peripheral vision, straight-on gaze.
Figure 5B:
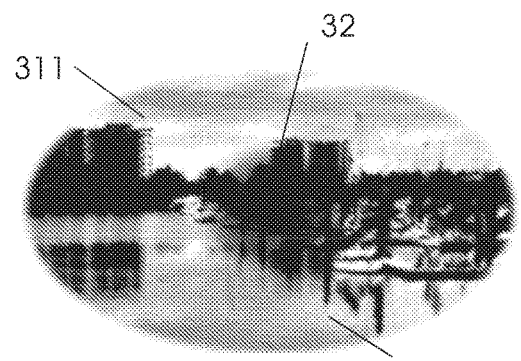

Remark: In all pictures the symbol denotes the gazing direction 12 on the display is indicated with the symbol illustrated in FIG. 2C.

Mapping and Monitoring of the Retinal Performance

The retina will be tested and mapped. According to our novel method, all the area of the retina will be scanned by a focalized stimulus while preventing the rest of the retinal locations from receiving any visual stimuli. Thus, the patient visual attention will be concentrated on the stimulus only. The performance of each retinal location will be evaluated and registered. The size, shape and number of the distinct areas can be determined for each subject according to the retinal condition.

Each retinal location will be tested for one or more of the following spatial and temporal parameters: visual acuity, reading acuity, reading speed, contrast sensitivity, crowding, reaction time, saccades, fixation stability, size of healthy area, color test, temporal JND (just-noticeable difference), orientation discrimination and/or optical distortions. The information, including test results with the time and date, will be recorded.

After attaining retinal mapping, the most suitable retinal locations for PRL (one or more) can be defined and registered. The mapping procedure can be repeated periodically in order to monitor the retinal condition—the location, the size and characteristics of this area can be modified according to the individual progress of the disease and the training paradigm.

The Basic Test Process

Figure 6A:
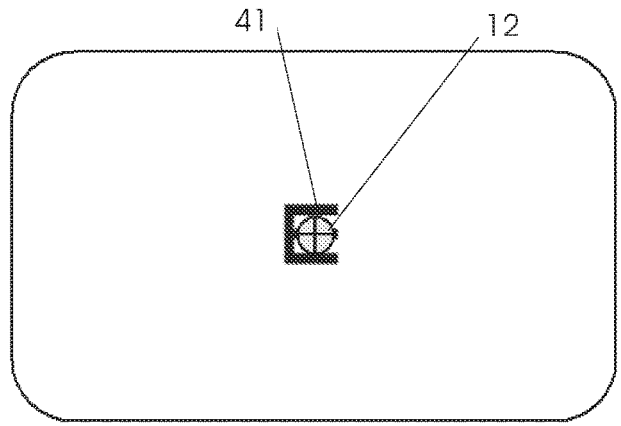
FIG. 6 illustrates a mapping phase, with target at center—no image perceived.
Figure 6B:
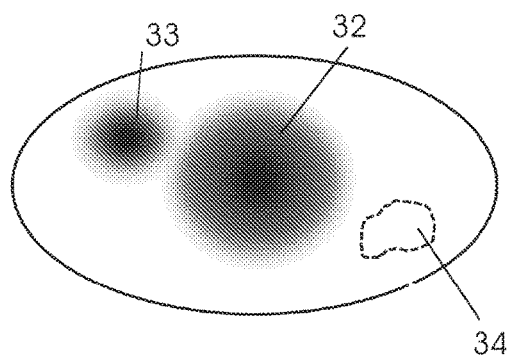

Let us assume that the patient has both a macular scotoma 32 and a peripheral scotoma 33, see FIG. 6B. Furthermore, let us assume that the patient has a PRL 34 at the location as shown. This PRL 34 is not known yet to the specialist performing the mapping test. The stimulus (e.g. as used on tumbling E charts) will be displayed on various locations on the display. The patient will be asked to identify the target orientation.

The patient will indicate when he sees a target and can fixate on the target either by using an input device such as a computer mouse button or by vocal feedback. This step can be done also without patient participation by analyzing the eye tracker data for fixation.

In FIG. 6A, the target 41 is located in the center of the display. The patient is gazing at the center of the display and, because of his macular scotoma 32, he sees nothing as shown in part B of this figure.

Figure 7A:
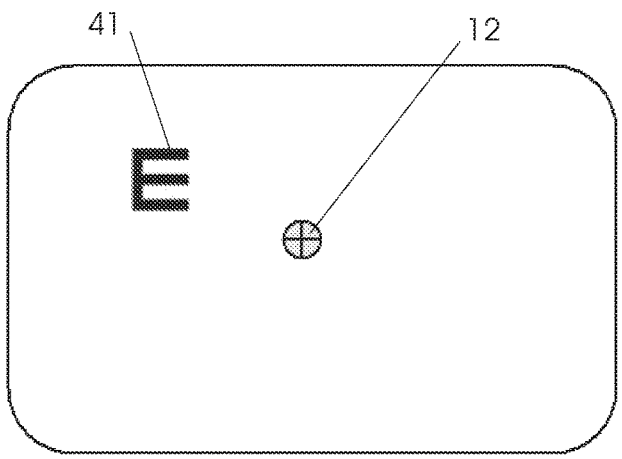
FIG. 7 illustrates a mapping phase, with target at left-up side—no image perceived.
Figure 7B:
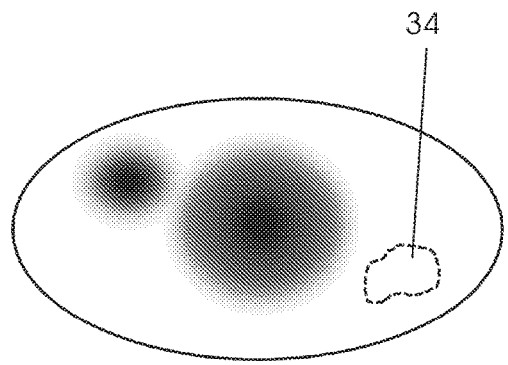

In FIG. 7A, the target 41 is moved to the left-upper side of the display. The patient is gazing at the center of the display but because of his peripheral scotoma 33, he sees nothing as shown in FIG. 7B.

In FIG. 8A, the target 41 is moved to the left-lower side of the display. The patient is gazing at the center of the display but, because of his general peripheral retina location which has a poor vision—he sees for example, a low resolution and contrast image 35 as shown in FIG. 8B.

In FIG. 9A, the target 41 is located at the right-lower side of the display. The patient is gazing at the center of the display but, because of his PRL 34 located there, he has a better vision than in the previous step (of FIGS. 8A, 8B) thus seeing a better image as shown in FIG. 9B.

Subsequently, the system moves the target 41B responsive to movements of the gazing direction 12, so as to keep the target 41B on the PRL 34, despite eye movements. See FIGS. 12A, 12B and 12C.

Additional Features of the Test

The mapping method can consist of different criteria, the decision on the best location for PRL could result from any of the criteria or a combination of a few of them.

Such criteria could be found by using tests like: Visual acuity, contrast sensitivity, reading speed, fixation stability, crowding, reaction time, saccades, size of healthy area, color test, temporal JND (just-noticeable difference), orientation discrimination and/or optical distortions.

Examples of some methods for performing some of these tests are listed below: The targets can be rotated in order to measure the visual acuity in multiple directions or orientations, as shown in FIGS. 10A and 11.

The targets can be displayed in different sizes in order to measure the best visual acuity in every part of the retina, as shown in FIG. 10B.

The targets can be displayed in different values of contrast and intensity in order to check the best sensitivity in every part of the retina as shown in part FIG. 10C.

The targets can be constructed in any shape, color etc. They can be animated for better acquisition by the patient.

In order to get reliable mapping results, it is critical that the location of the test targets will be at a fixed location in relation to the patient's gaze. This is usually done in current tests 10 by asking the patient to fixate on a fixation point while measuring his peripheral vision.

However, the patient, especially at the early stages of the disease, has a tendency to move his (damaged) straightforward gazing direction on to the target, rather than using the (better vision) PRL.

Thus, the peripheral vision through the PRL may be destroyed, without achieving any vision improvement, because of the macular scotoma 32.

By using the eye tracker, the location of each target 41B on the display will be fixed in relation to the gazing direction 12, i.e., when the patient changes his gazing direction 12 during the test, the target 41B will move accordingly, thus ensuring that the stimulus, for each test, will be on a stationary location on the retina. See FIGS. 12A, 12B and 12C.

A stationary stimulus will significantly improve vision (otherwise the image may be blurred); improved vision using our new system and method may result in further vision improvement by the patient in response, as patient's body collates together sensor cells and neurons for the PRL 34 at that location. Thus, a therapeutic effect may be achieved, wherein the body heals itself, aided and stimulated by our system and method.

Figure 13:
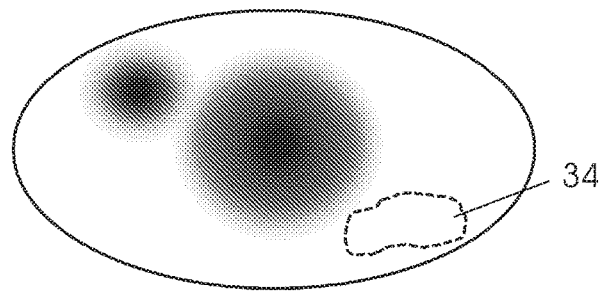
FIG. 13 illustrates a mapping phase—PRL determination.

Using the eye tracker, the BCEA ellipse will be evaluated and scored. Each location will be assessed, quantified and scored to determine the best PRLs—see FIG. 13.

Training Method

One of the main objectives of the present invention is to train the patient in using a PRL, or to help the patient to develop a PRL in a predefined, constant and limited area of the retina which is the patient's retinal location with the highest potential to become a "pseudo-fovea".

Figure 14A:
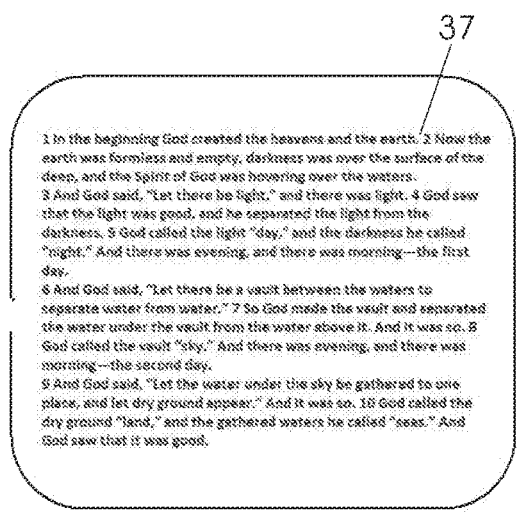
FIG. 14 illustrates a training phase—eliminating crowding on display.
Figure 14B:
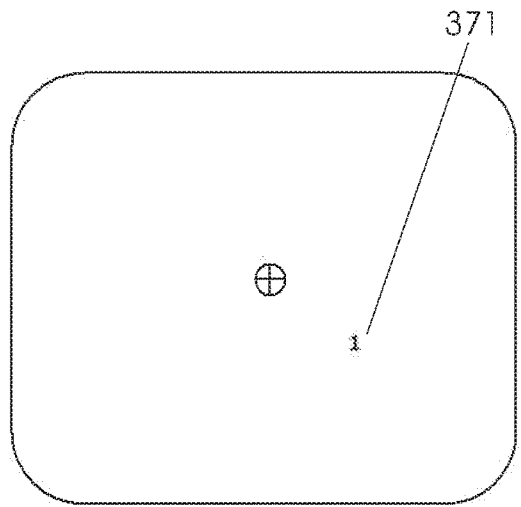
Figure 14C:
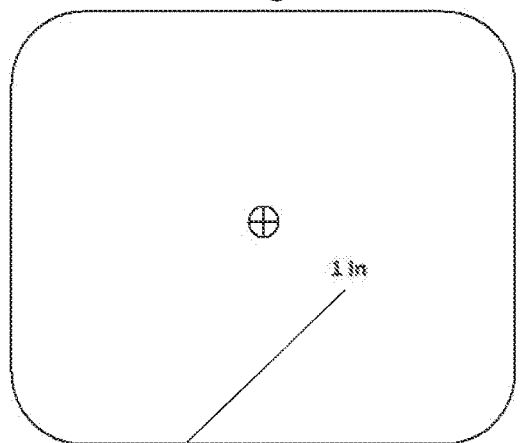
Figure 14D:
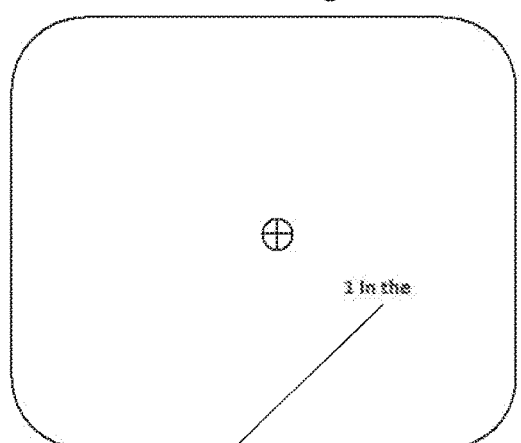

Instead of using a target image that has a visual information covering the whole area of the display (see FIG. 14A), the new system presents only limited information corresponding to the PRL (see FIGS. 14B and 14C), while preventing exposure of visual information from the rest of the retina.

This "non-crowded" stimulation system and method will shorten the patient's learning curve, by eliminating "competing" areas of the retina which may otherwise intervene in the process of the PRL training. This system and method will also improve patient's vision fixation stability, and in general will ease up the process.

The masking of the unnecessary information could be done in different ways such as a fixed color mask, gradient color changing mask, blurred image, etc. See FIG. 15.

The location of the focalized stimulus is stabilized on the retina with the aid of eye trackers—that is, if the gazing direction changes, the focalized stimulus will move correspondingly, so as to keep the stimulus on the same location on the retina. Otherwise, the stimulus may appear as an indistinct blur and mapping may be hindered or may be impossible to perform.

The trained parts of the retina, comprising either a single PRL or multiple PRLs, will be based on the mapping system explained above or supplied by any other measurement techniques. This will provide the patient a steadier fixation point. This technique will prevent the need of constant searching for the best location for a fixation point.

Figure 16A:
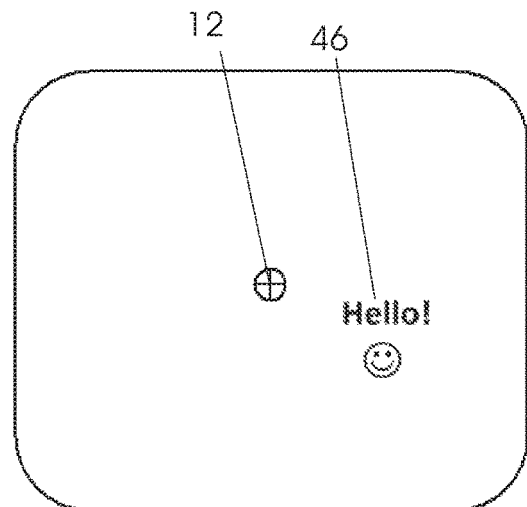
FIG. 16 illustrates a training phase—constant PRL location on display using eye trackers.
Figure 16A:
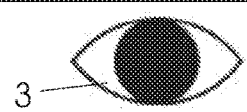
Figure 16B:
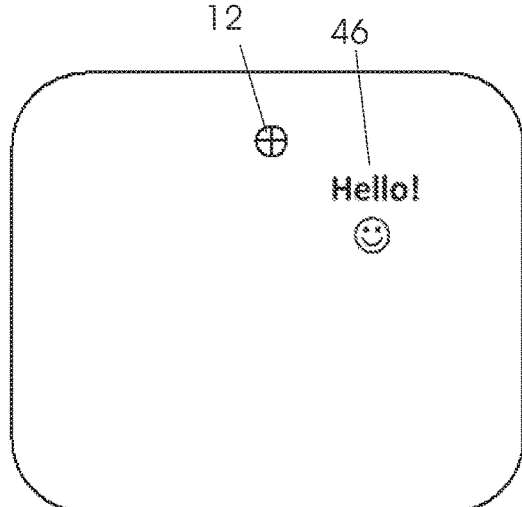
Figure 16B:
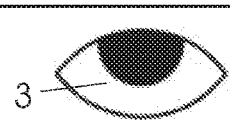
Figure 16C:
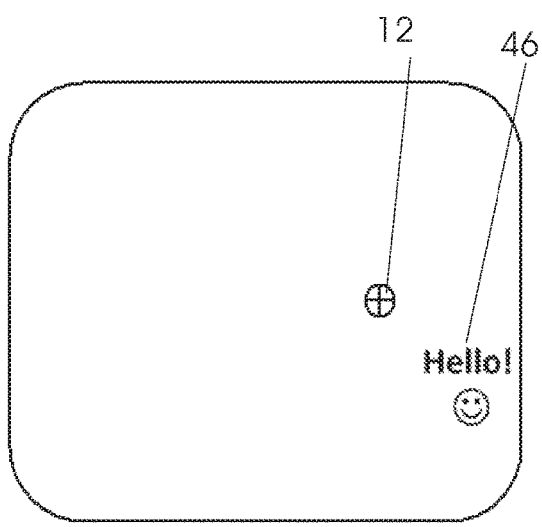
Figure 16C:
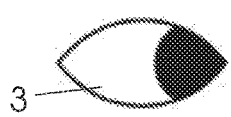

In order to ensure the image information on a constant retinal location, the displayed image on the monitor corresponding to the PRL follows the eye gaze in real time—see FIGS. 16A, 16B and 16C. The information regarding the eye gaze (the gazing direction 12 for each eye) is received from an eye tracking device composed of a video camera and appropriate software or any other commercial eye tracking device.

Alternative Training Method

Following is a description of another embodiment of the training method, see FIG. 22.

Unlike the abovedetailed training method, the target will not move with the change in the gazing direction, rather only the mask will move according to the gazing direction. The system will mask/deteriorate the entire image except the location of the desired good PRL. If the patient is gazing straight ahead, then only the lower/right part of the image will be displayed on the PRL area while the rest of the image will be deteriorated or completely masked away. See FIGS. 22A and 22B.

If the patient is gazing up and left, only the middle part of the image will be displayed on the PRL area (which is now in the center of the displayed image) while the rest of the image will be deteriorated or completely masked away. See FIGS. 22C and 22D.

Stimulating a retina constant location with the visual information will force this location to serve as the fixation point, since once eye gaze is changed, the eye tracking function will move the exposed area on the screen accordingly, thus preserving (exposing the image onto) a fixed area on the retina. Using the same location to fixate can serve as a training procedure, leading to an improvement in performance and subsequently enabling for this location to serve as "pseudo-fovea".

The patient will gain better fixation stability, visual acuity and contrast sensitivity performance. The area of the PRL can be determined by the size of the exposed visual information area, this area can be modified along the training, starting from a large area and narrow it, or the opposite—use a small area at the beginning and then stretch it.

In case where more than one PRL exists, this training method will force the patient to abandon his secondary locations and train the brain to develop only one primary PRL This will prevent confusion and the need to search for the best location.

Basic Training Process

PRL is defined through the mapping progress as described above, or by any other method.

1. Different masking methods (different colors, gradient, blurring, etc.) may be displayed to the patient to find his preferred method.
2. Different sizes and shapes of unmasked retinal areas may be displayed to the patient around his PRL to find his preferred shape, taking also in account the best size and shape for PRL training.
3. The mask will follow the eye tracking data as to preserve a fixed location of the exposed data on the PRL area. The patient will be asked to perform visual tasks, such as reading, smooth pursuit of a moving target, saccades from point to point, etc., while using his PRL for a predetermined time. This process will be repeated according the training program.
4. The system will record eye tracker data such as gaze direction, speed, pupil size, saccades, micro-saccades, tremor, etc.

The system will analyze the progress by calculating and analyzing gaze change speeds, BCEA etc., will score the results and provide feedback to the patient/specialist. Based on the patient progress, the system will automatically decide when to change the various task parameters and enhance the training or terminate it.

Some of the central retinal diseases are progressive. As a result, the PRL may change its position due to a progress of the disease. Since our method enables constant monitoring of the retinal performance, a reduction in the current PRL performance might lead to a new training for the next most suitable location for the next PRL.

Forcing the patient to use a single, constant location for viewing may be used in standalone training.

Other, prior art trainings techniques, can also be used in combination with the proposed method to enhance the development of the "pseudo-fovea".

Reducing visual crowding and visual noise from the visual stimuli by masking the area around the "pseudo-fovea" (either on the screen or the goggles) might be used not only in the training sessions described in this document, but rather in other normal activities performed by the patient such as reading, internet browsing, watching TV, handcrafting, writing, playing, etc. This way, the PRL development will be further enhanced.

Apparatus

Our novel method of training on a constant retinal location and limiting the visual information from the rest of the retina can be implemented in either one of two configurations, or in a combination of the two: a stationary (desktop) system, and a portable system with a wearable device such as goggles.

1. A stationary (desktop) system, in front of a computer display, where the entire image on the display 51 is masked around the target 41B corresponding to the PRL area.

Figure 17:
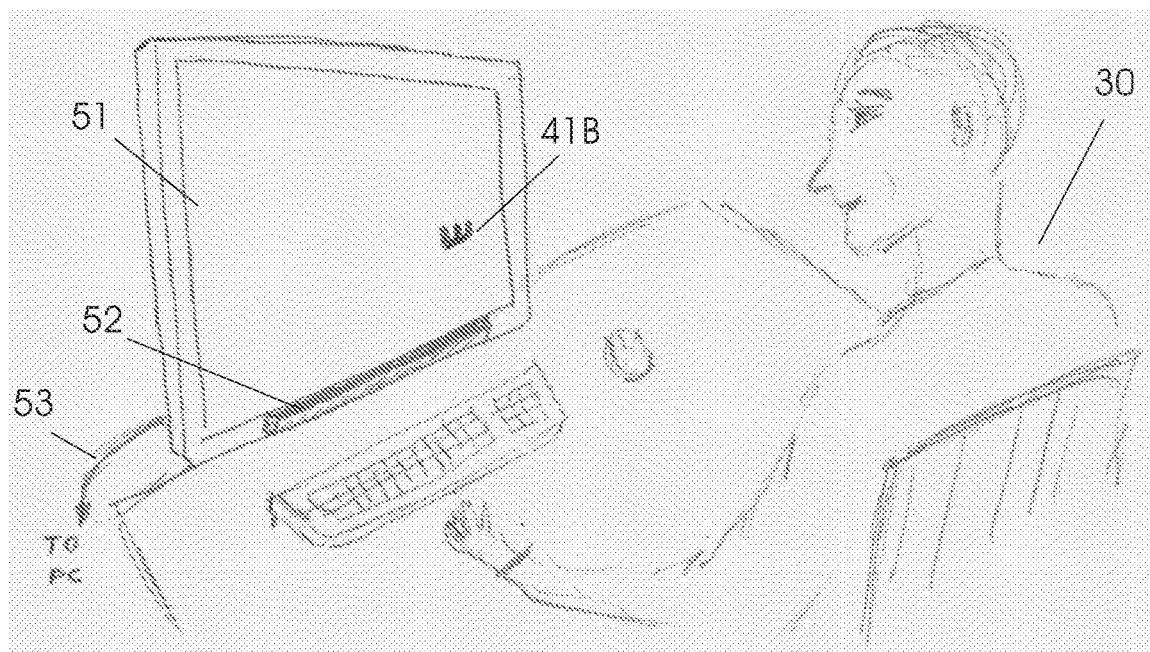
FIG. 17 illustrates a stationary (desktop) system basic setup.

In FIG. 17, the patient 30 sits in front of a display 51.

The system comprises a display 51, one (remote) or two (near the eye) eye trackers 52 (for each eye separately). The display 51 includes a link 53 to a computer such as a personal computer (PC).

Figure 18:
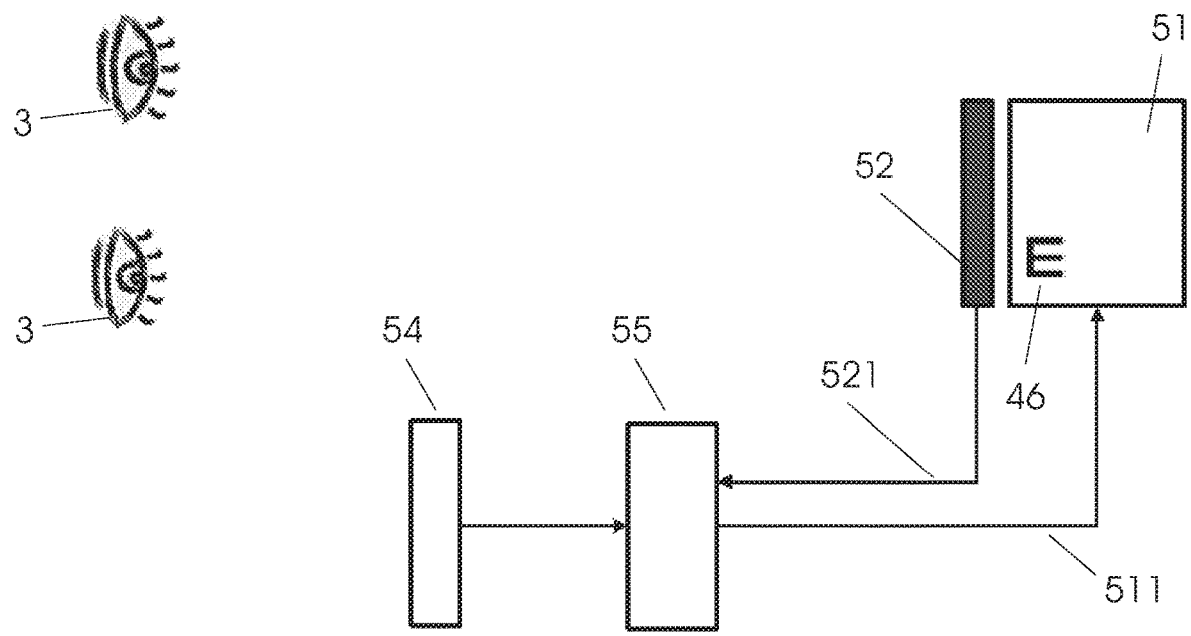
FIG. 18 illustrates a stationary (desktop) system block diagram.

FIG. 18 shows a block diagram of the stationary (desktop) system, which includes a display 51, connected to a processor 55. Also shown is the link 511 conveying display signals from the processor 55 to the display 51.

The display 51 can be a part of a PC, laptop computer, tablet, smart phone, television (TV) or the like. The software is programmed in the processing unit memory.

The system further includes remote eye tracker means 52 for measuring the gazing direction of each eye. Signals 521 conveying in real time the gazing direction of each eye in two dimensions (azimuth and elevation) are transferred to the processor 55.

If the patient is using glasses for optical correction for viewing the computer screen, he should use them during the training as well.

If the retinal damage of the two eyes is significantly not symmetrical, a different PRL location will be tailored to each eye.

In this case, a prism might be added to at least one side of the patient glasses, and the patient will use the prismatic spectacles also during the training. Alternatively, the patient might refrain from using the prismatic glasses and in this case a 3D system will be used (3D glasses and 3D screen) to separate the PRL stimulus to each of the two eyes.

2. A portable system with a wearable device such as goggles 6, see FIG. 19.

In one preferred embodiment, a portable system comprises goggles 6 and a processing unit 61. The processing unit 61 can be reduced in size and thus embedded in the goggles 6. In the configuration as shown, the processing unit 61 is in a separate unit which is attached to the patient's belt, to reduce the weight of the goggles 6.

Figure 20:
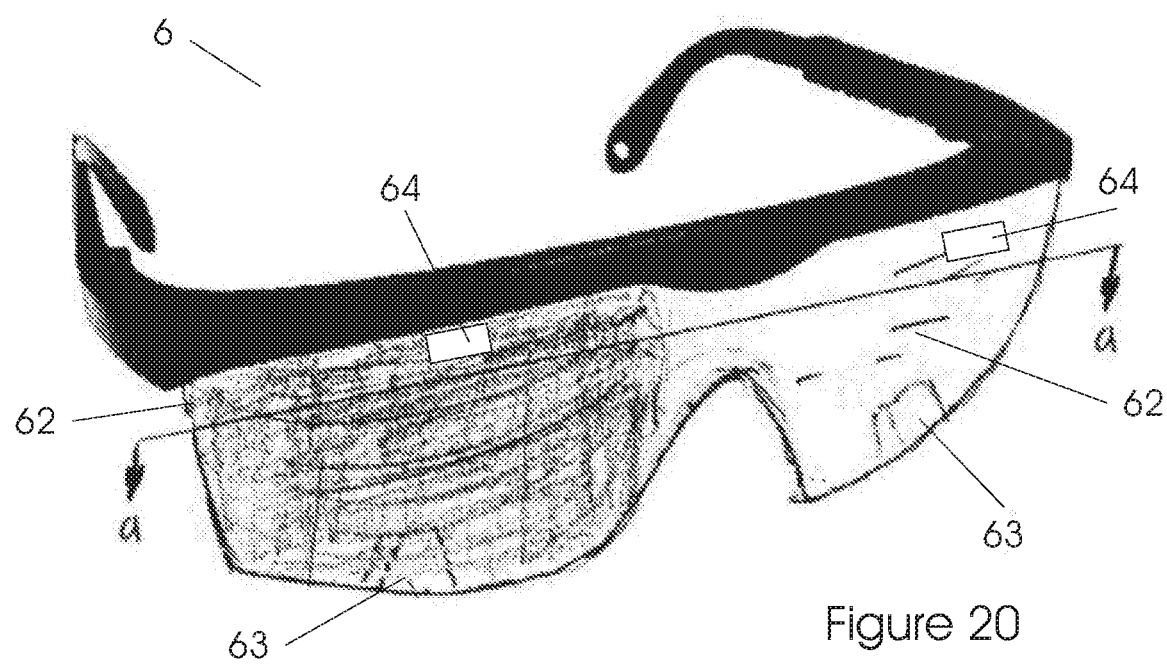
FIG. 20 illustrates a goggles system near view.
Figure 21:
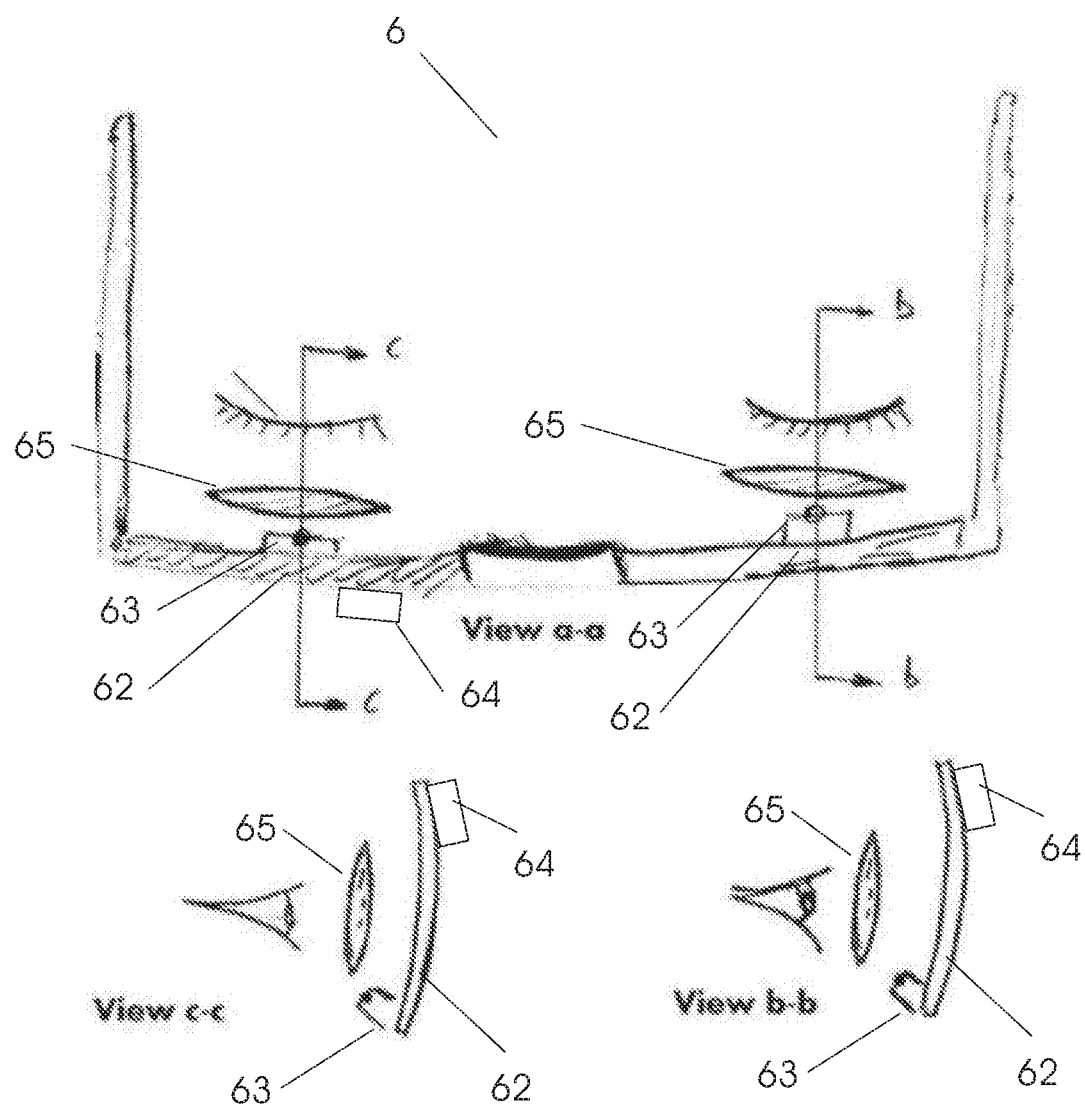
FIG. 21 illustrates a goggles system cutaway views.

In the embodiment illustrated in FIGS. 20 and 21, the system comprises one or two micro displays 62 (one for each eye separately), one or two eye trackers 63 (for each eye separately), corrective optics 65 if necessary, and a processing unit (not shown). Furthermore, the system includes a camera 64, or two cameras 64, one for each eye. The video of these scene cameras will go through all the processing explained in the present disclosure.

The various components of the system are attached to the goggles 6 frame as shown. The software may be stored in the processing unit's memory.

If the two eyes are significantly not symmetrical in terms of the retinal damage, optional advantageous would be to develop a different PRL position in each eye.

In this case, a prism (not shown) might be added to at least one side of the patient glasses, and the patient will use the prismatic correction optics also during the training.

Alternatively, the patient might refrain from using the prismatic glasses and the PRL stimulus will be presented at different locations for the two eyes separately on the two displays accordingly.

The above description refers to a method wherein correction and/or treatment is applied concurrently to each of the patient's eyes.

In another embodiment, only one eye will receive treatment and/or correction, whilst the other eye will look without any such improvements. Preferably, the eye with the better vision will receive correction and/or treatment.

Eye trackers are well known devices, which are used for various applications in a variety of fields. They measure the gazing direction, gazing speeds, pupils size and more. They can provide this data for one eye or for each of the two eyes.

Main Objects of the Present Invention

1. To map the best location for the patient's PRL by using eye-tracking and various criteria or a combination of a few criteria.
2. To ensure the patient's PRL is located at the optimal location.
3. To enhance the development of a "pseudo-fovea" at the most suitable PRL location.
4. To improve visual performance such as fixation, stability, saccadic movements, contrast sensitivity, visual acuity, reading speed and others.
5. To avoid patient's constant search for the right fixation point.
6. To reduce crowding by eliminating information from being presented on locations other than the PRL.
7. (Optional) To reduce visual noise by eliminating non relevant information from being presented on other retinal locations than the PRL.
8. To improve fixation stability and reduce the BCEA size.
9. To monitor the performance of the PRL to provide feedback for PRL training.
10. To monitor the performance of the PRL to decide if a new PRL should be found and trained.
11. To identify the best location for developing new PRL in case of degraded retinal performance and/or provide suggested foveal location with the best VA.
12. In case of performance reduction of the existing PRL, to train the patient in using the next most suitable one more effectively before the existing PRL is totally damaged.

Main Benefits of the Invention Over Existing Instruments and Methods

1. The new method offers a reliable accessible retinal mapping, monitoring and training for low vision patients with pathologies that affect the central retina. The retinal mapping, monitoring and training can be performed either at the patient location e.g. at home, at the clinic, or by using the goggles system, the training can be performed anywhere.
2. Ease of use: The operation of mapping, monitoring and training are very easy to use since all tasks are done with a constant PRL location as ascertained by eye tracking, in such a manner that prevents confusion with information from other retinal locations.
3. Reduce confusing visual clutter: Prior art methods for PRL training present a complete image to the patient, and use visual awareness, biofeedback using an eye tracker or practice in magnified text reading. This may confuse a patient, especially one with deteriorated vision.

The new method, however, limits the visual information projected on the retina to only a predefined location (PRL). Eye tracking information is used to move the displayed image for the PRL (or image masking outside the desired PRL) on the monitor to follow the patient gaze, thus preventing the visual information from other areas outside the PRL.

4. Optionally, any prior art trainings PRL method may be used in combination with the new method of eliminating the information from the rest of the retina.
5. Prior art methods for locating the most suitable PRL use dedicated equipment which is available only at the specialist clinic, such as visual field tests or scanning laser ophthalmoscope. The new method can be performed at the patient's home using inexpensive equipment including personal computer, eye-tracker (video camera) and software.

Vision Improvement Method

In one embodiment, the new method comprises the steps of:

1. Mapping the retina performance;
2. Identifying the most suitable location on the retina for developing a "pseudo-fovea";
3. Training the most suitable location on the retina, to develop a "pseudo-fovea"; and
4. Monitoring the retinal performance, giving warning regarding changes in performance that might indicate a deterioration in the retina health.

Additional details, as well as other embodiments of the present invention are detailed below.

Modes of Operation of the Display System

Figure 23:
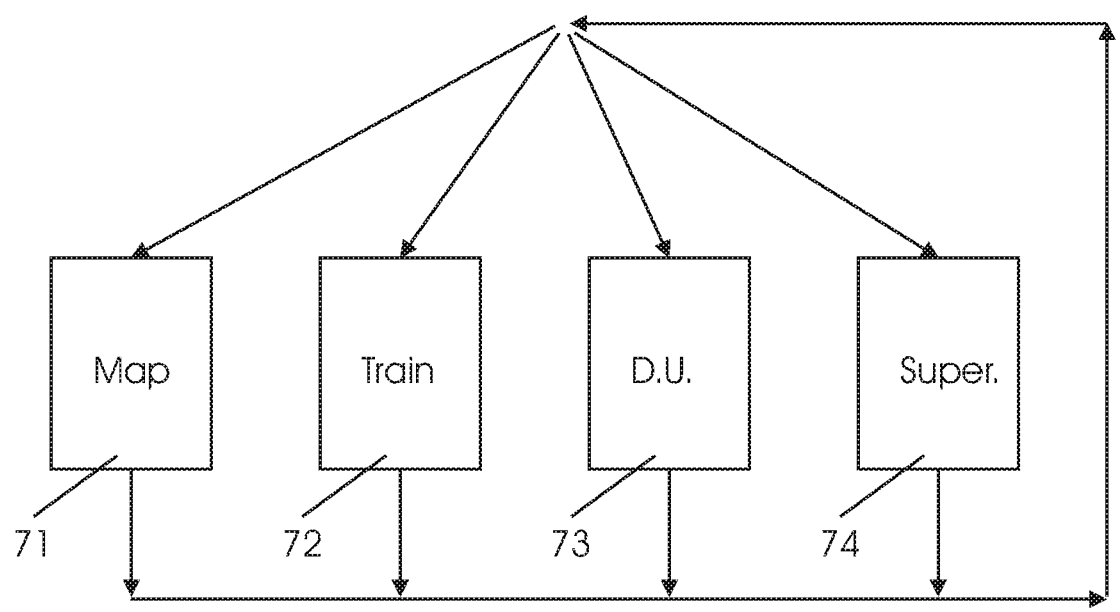
FIG. 23 illustrates a method for activating modes of operation in the display system.

Referring to FIG. 23, the user can activate any of the modes of operation in the system. The modes of operation include Mapping, Training, Daily use and Supervisor/Monitor.

a. Mapping 71—the retina of each eye is tested and mapped, to find the most suitable retinal location for PRL. This location is then defined and registered, for subsequent use as well as use in the other modes of operation of the system.

The PRL may be used to replace the damaged macula for use in reading and everyday life. FIGS. 1 to 13 and the related text detail operation of the system in the Mapping mode.

Mapping may be performed using the system and method disclosed in the present invention, or using prior art methods.

In either case, the location of the PRL 34 is stored in the system and is available in all the modes of operation therein.

The result of mapping: two angular coordinates (azimuth and elevation) in a polar coordinate system, indicative of the location of the PRL 34 on the retina, with respect to the gazing direction 12 (for example see FIGS. 6 to 9, and 11 to 13).

A stationary system usable for Mapping is illustrated in FIGS. 17 and 18 and the related text.

Alternatively, a portable, wearable embodiment of the display system may be used in the Mapping mode. See for example the embodiment illustrated in FIGS. 19 to 21 and the related text.

b. Training 72—in this mode, the PRL found in the Mapping mode is stimulated so as to strengthen it, to further improve the patient's vision.

Figure 15A:
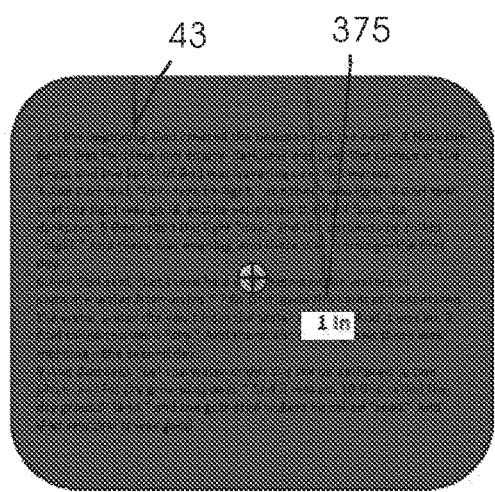
FIG. 15 illustrates a fixed color mask, gradient color changing mask.
Figure 15B:
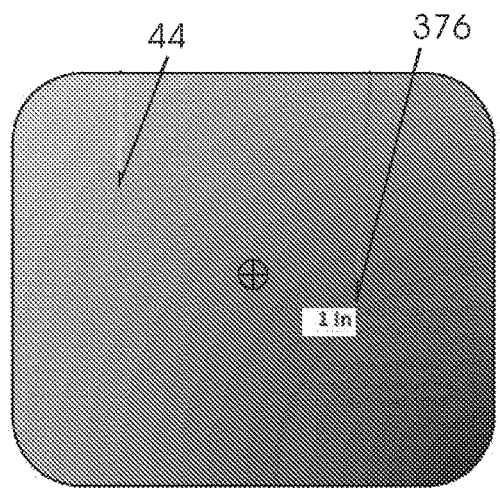

Training methods are detailed with reference to FIGS. 14 to 16 and the related text.

In Training mode, new vision-related connections are formed, thereby improving the patient's vision using the PRL.

The stationary system illustrated in FIGS. 17 and 18 and the related text may also be used in Training.

The portable, wearable embodiment of the display system may also be used in the Training mode. See for example the embodiment illustrated in FIGS. 19 to 21 and the related text.

c. Daily use 73—the patient may enjoy improved vision using the PRL found in the Mapping mode and enhanced in the Training mode.

The new, portable, wearable embodiment of the display system may be used to further improve the patient's vision during daily use. See for example the embodiment illustrated in FIGS. 19 to 21 and the related text.

Even without the display system, the patient may enjoy improved vision as a result of activities of the display system in the Mapping and Training modes.

d. Supervisor/Monitor 74—in this mode, past activities and patient's performance log may be reviewed and evaluated, and system's parameters may be adjusted responsive thereto, to adapt the system to the patient's characteristics, so as to achieve better results.

Referring to FIG. 23, the user can activate any of the modes of operation in the system: Mapping 71, Training 72, Daily use 73, and Supervisor/Monitor 74.

In the embodiment of the invention as shown, it is possible to switch from any mode of operation, to any other of the four modes.

Figure 24:
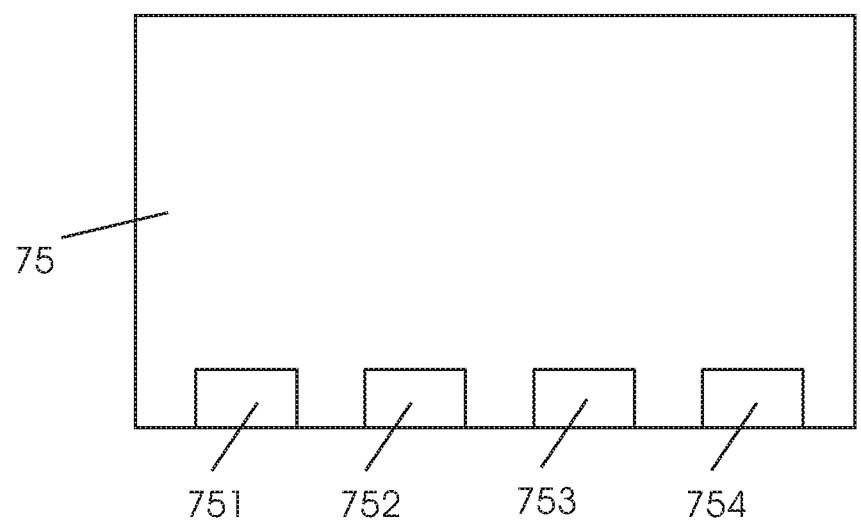
FIG. 24 illustrates a human-machine interface for setting the system's mode of operation.

FIG. 24 illustrates a human-machine interface for setting the system's mode of operation. The computer display 75 which implements the interface may be presented to the user (i.e. a patient or a therapist), in any of the modes of operation shown in FIG. 23.

Icons 751, 752, 753 and 754 presented on the display 75 may be used to activate any of the modes of operation: Mapping 71, Training 72, Daily use 73, and Supervisor/Monitor 74, respectively.

With the passage of time, as the patient's vision further deteriorates, the area of the retina used for PRL itself may become damaged; the Mapping mode 71 may be re-activated, to find a new PRL.

The mapping procedure can be repeated periodically in order to monitor the retinal condition—the location, the size and characteristics of this area can be modified according to the individual progress of the disease and the training paradigm. Multiple PRLs can be mapped and used.

Figure 25:
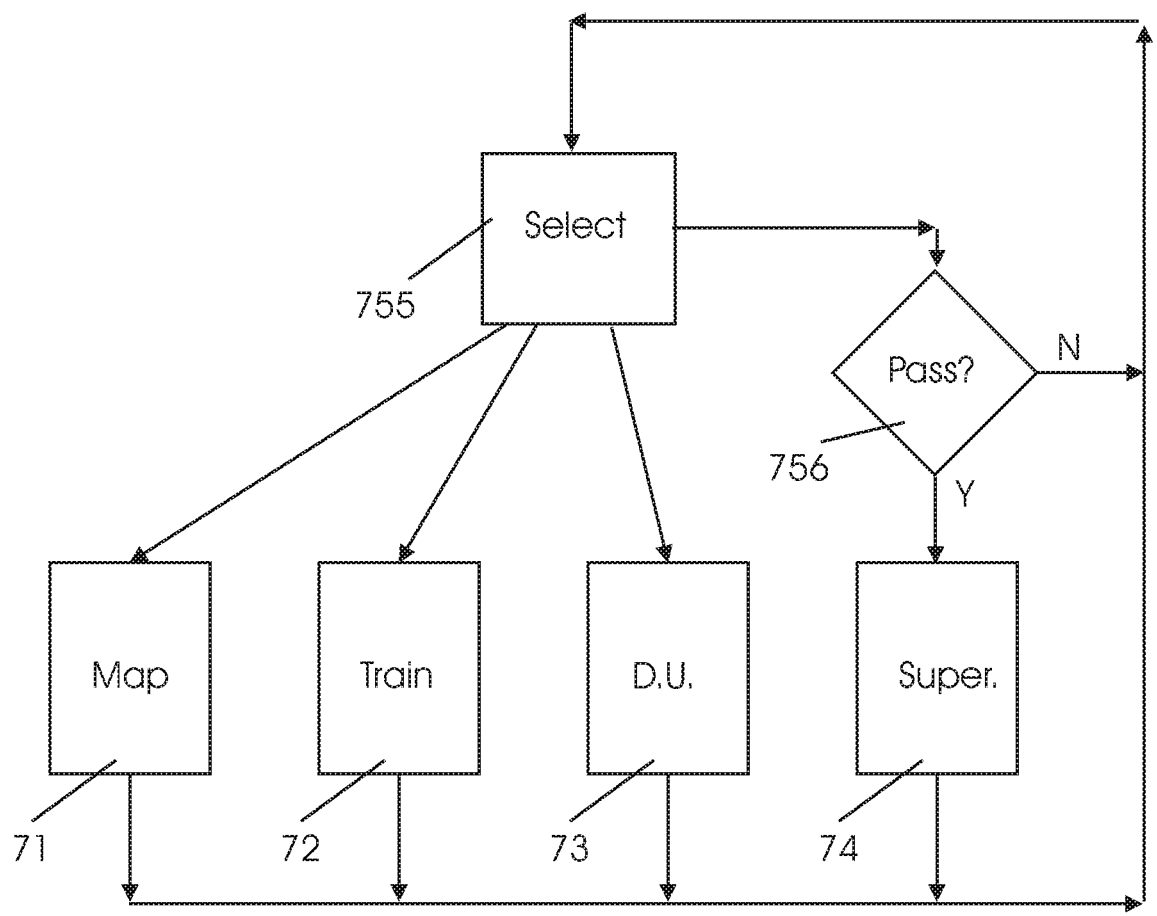
FIG. 25 illustrates another method for activating modes of operation in the display system.

FIG. 25 illustrates another embodiment of a method for activating modes of operation in the display system. In this embodiment, the Supervisor/Monitor mode 74 is protected so as to prevent or minimize the possibility of misuse of the system by unauthorized persons.

The rationale for this method is that the display system collects and stores private, confidential information about a patient; this information should be protected. Furthermore, setting the parameters of operation of the display system may require knowledge and experience, which a therapist possesses, and the patient—not.

Thus, three modes of operation may be freely activated: Mapping 71, Training 72, and Daily use 73. The Supervisor/Monitor mode 74, however, requires a password for its activation; only if the user gives the correct password in the Guardian module 756, the Supervisor/Monitor mode 74 is activated.

Another improvement in the method illustrated in FIG. 25 is a Select module 755. When a user desires to change the mode of operation, a menu for supporting the user in this task is presented. The menu may include icons for activating the various modes in the system, may recommend preferred actions and/or may display Help messages.

According to user's choice, any of the abovedetailed modes of operation may be activated.

Another improvement in the method illustrated in FIG. 25 is an Activity Log module 757. This module operates concurrently with any mode of operation of the system, to measure any activity performed by the display system and store it for subsequent use.

Using hardware embodiments with the 4 modes of operation

The stationary embodiment disclosed with the FIGS. 17 and 18 and related description may be used with the following modes of operation: Mapping 71, Training 72, and Supervisor/Monitor 74.

An obvious limitation of the stationary system is that the user cannot take it with him/her, therefore use in the Daily use mode 73 may be severely limited or impossible.

Figure 19:
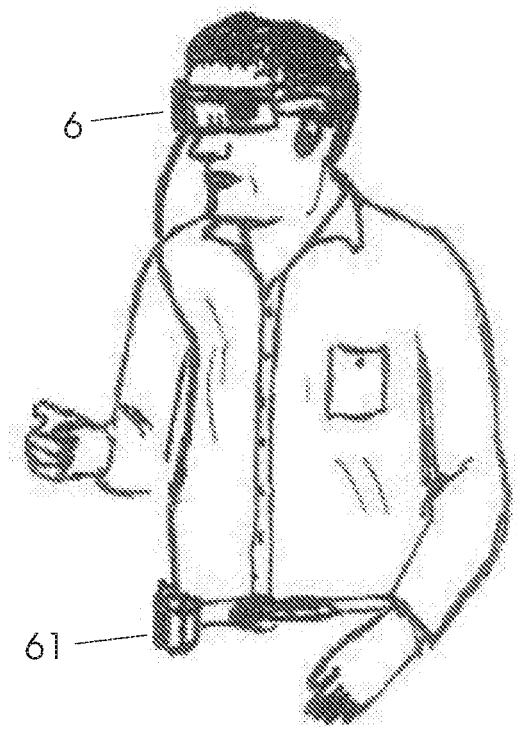
FIG. 19 illustrates a goggles system general view.

The portable/wearable embodiment disclosed with the FIGS. 19 to 21 and related description may be used with all the modes of operation: Mapping 71, Training 72, Daily use 73, and Supervisor/Monitor 74.

In Supervisor/Monitor 74 mode, input means such as a keyboard, keypad, pointing device, etc., are necessary; such means may be connected to the display system using a connector such as micro-USB, or via a wireless link such as Wi-Fi or Bluetooth.

In another application, a therapist may use a stationary system, and the patient—a portable system, wherein the two systems can connect to each other.

Method of Operation:
   a. Connecting the stationary and the portable systems.
   b. The portable, personal system transmits present settings, and a log of patient's activities.
   c. The therapist reviews the information on his stationary system and plans future therapeutic sessions.
   d. The parameters of the portable system are adjusted if necessary.
   e. The stationary and the portable systems are disconnected from each other.

Another Method for Detecting the PRL in the Mapping Mode

Figure 26:
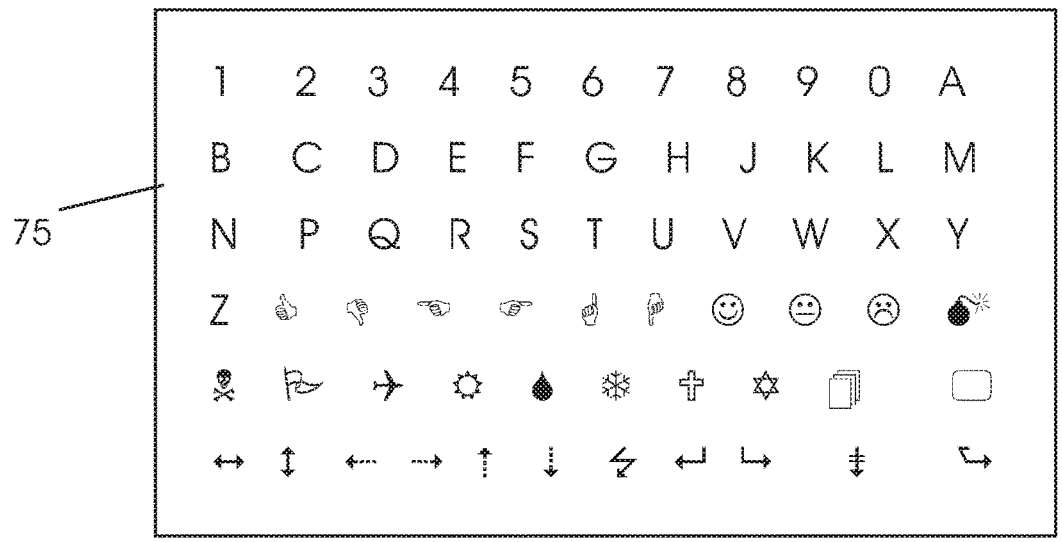

This method is another embodiment of the Mapping mode methods described with reference to FIGS. 6 to 13. The method comprises:
   a. Presenting a display 75 on the whole, or a large part of, the area of the retina; the display includes a plurality of unique characters (each character appears only once on the display). The characters may comprise alphanumerics and/or other symbols, as illustrated in the example in FIG. 26.
   b. The display of Step (a) is presented to only one eye at a time.
   c. The display of Step (a) is stabilized on the retina using a closed loop servo system with an eye tracker device for measuring eye movements, see FIG. 27. Actually, there are two independent loops being closed, one for azimuth, the other for elevation.
   d. The therapists asks the patient "What do you see?".
   e. The patient's answer, i.e. "I see the number 7" indicates unambiguously the location of the PRL—the area on the retina offering a relatively better vision.

Rationale and Technical Details
   a. For patients whose macular area is damaged, as illustrated for example in FIGS. 4B, 5B, 6B, etc., they look at the display of FIG. 26 with their peripheral vision, see FIG. 1.
   b. The PRL on the retina serves as a bi-dimensional band-pass filter in this application, as illustrated with reference to FIGS. 8 and 9. The patient will not see the characters presented on damaged areas of the retina, such as in FIG. 8. The patient will see the character presented on the PRL area of the retina, such as in FIG. 9.
   c. The eye tracker measures the direction of the gazing direction 12, as shown in FIGS. 1 to 9, 17, 18 and 21. Thus, the display system can correlate the characters presented on display 75 with the patient's answer and the measured gazing direction 12, to find the angle of the PRL in two angular dimensions, relative to the gazing direction.

For example, a PRL measurement may give the following result:
   For Left eye, PRL=+21.5 degrees el, −11 degrees az
   For Right eye, PRL=+13 degrees el, −15 degrees az
   d. People having vision deficiency such as a macular scotoma 32 (see FIG. 6B) may have difficulty stabilizing their gazing direction 12; that is, the gazing direction will change involuntarily and uncontrollably, despite patient's best efforts to look in only one direction.

These changes may cause the display to appear fuzzy to the patient—rather than one character being presented on each location, each character will be projected onto various locations on the retina, so the character presented on each location will change. This may hinder the PRL detection, or may render the whole Mapping process useless.

Figure 27:
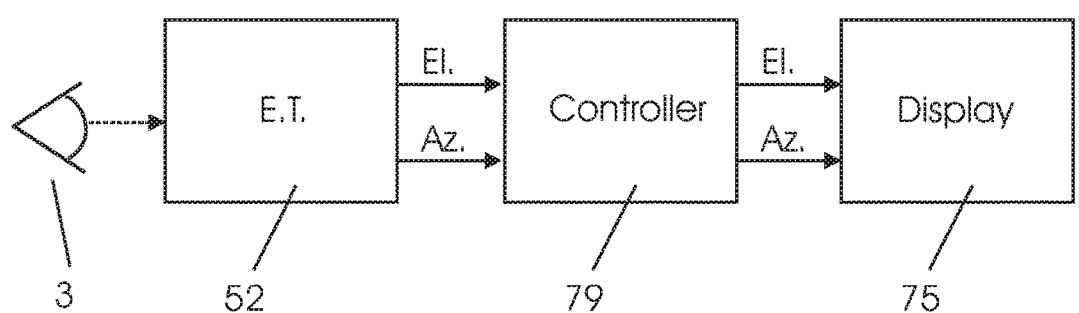
FIG. 27 illustrates gazing direction stabilization using an eye tracker in a servo loop.

To address this problem, the display projected on the retina is stabilized in two angular dimensions, using the system of FIG. 27. This system allow for each character to be continuously presented on a fixed, specific location on the retina, despite eye 3 movements. The eye tracker 52 measures the gazing direction of the eye 3 and outputs two signals indicative of the direction angle in azimuth and elevation. The controller 79 moves the displayed text and/or images on the display 75 in such a way, that the images are projected on the same locations on the retina, despite eye movements.

In other words: as the gazing direction changes, the characters on the display 75 are moved accordingly, so the same characters will be displayed on the same locations on the retina. See also examples in FIGS. 16A, 16B and 16C.
   e. The closed loop servo system may be designed using methods and technologies known in the art, but taking into account the unique properties of the human eye.

For example, either analog or digital loops may be used. The control loop may be of the first order, second order or a higher order. Either a linear or a nonlinear system may be implemented.

Adaptive or optimal control technologies may be used.
   f. If there are more than one PRL locations, the patient may report that he sees two or more characters; further measurements may be then performed, to find the best location for the PRL.

Display Stabilization in the Various Modes of Operation

The servo loop illustrated in FIG. 27 should operate differently in the various modes of operation of the display system, as detailed below.
   a. In the Mapping mode 71 and Training mode 72, the control loop is so closed as to suppress or minimize any changes in the location of the characters displayed on the retina, despite eye movements.

Figure 28:
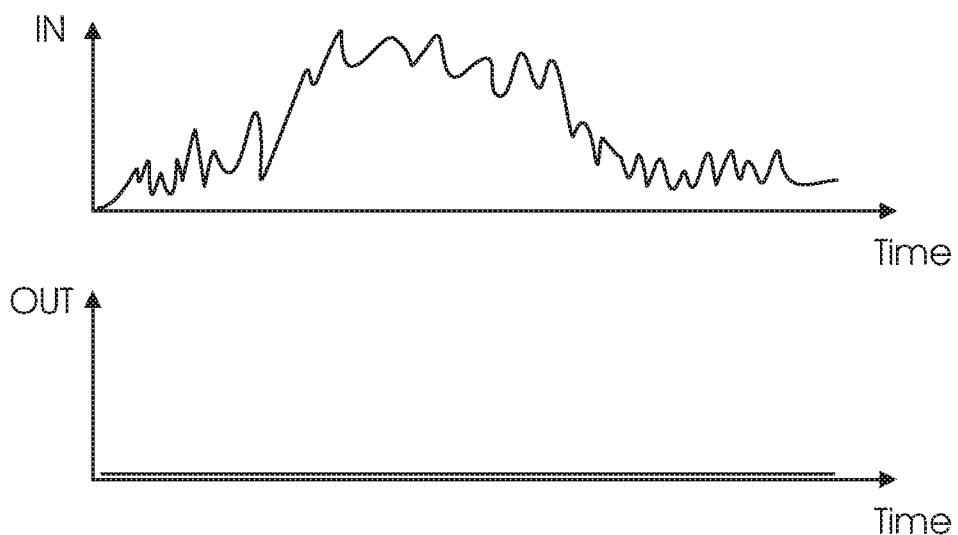
FIG. 28 illustrates the operation of the servo loop in the Mapping and Training modes.

Basically, in this mode all eye movements are considered an interference, to be supressed. FIG. 28 illustrates the operation of the servo loop in this mode.

Figure 29:
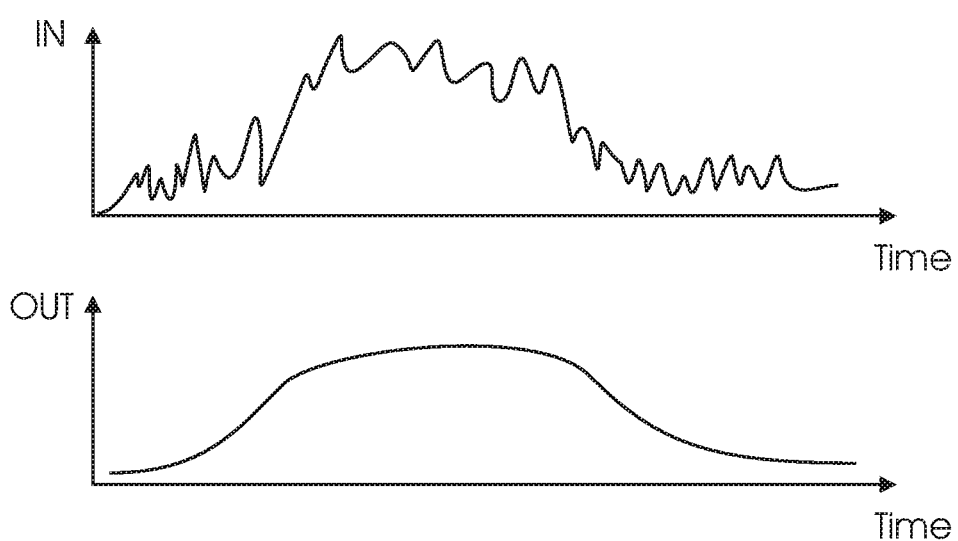
FIG. 29 illustrates the operation of the servo loop in the Daily use mode.

In both FIGS. 28 and 29, the IN graph indicates angular eye movements in one dimension; the OUT graph indicates the movement of the image on the retina, corresponding to the angular eye movements.
   b. In the Daily use mode 73, the loop is closed so as to distinguish between random variations in the gazing directions and voluntary eye movements, when the patient desires to look in another direction.

The loop so acts as to supress random/undesired variations in the gazing directions, whereas not affecting voluntary/desired eye movements.

Basically this mode is akin a bidimensional Low Pass Filter LPF.

FIG. 29 illustrates the operation of the servo loop in the Tracking/LPF mode.

Benefits:
   a. In the Mapping mode 71 and Training mode 72, an augmented image is presented to the patient, wherein characters or figures have each a fixed location on the retina; thus, the image is clearer and less fuzzy.
   b. In the Daily use mode 73, the image on the retina will change when the patient so desires—that is, when the patients wishes to look in another direction.

Still, a better image is presented to the patient, because random, noise undesired eye movements are filtered out—when looking in any direction, the patient will be presented with a clearer, less fuzzy image.

Using a 3D System Technology

In the present invention, components of a 3D system (3D glasses and 3D screen) are used in an unconventional way: not to present a 3D image to the user, rather to separate the PRL stimulus to each of the two eyes.

In the Mapping mode 71 and Training mode 72, the image displayed onscreen is intended for only one eye at a time; 3D glasses, acting as an optical ON/OFF switch for each eye, allow to present the image to only one eye at a time, as desired.

Examples of images usable in the Mapping mode 71 and Training mode 72 are shown in FIGS. 6A, 7A, 8A, 9A, 10, 14 to 16, and 26.

Moving the Image on the Screen According to the PRL Location

An essential aspect of the present invention relates to moving the image on the screen (display) according to the PRL location.

Benefit: Ease of use, so that the patient will not have to adopt awkward eye/head positions.

In Mapping mode, the PRL may be detected using the method as detailed for example with FIGS. 9 and 11—the target 41 is shown on the screen so it will be projected onto the PRL region 34, wherein the gazing direction 12 points conveniently at the center of the display.

FIGS. 12A, 12B and 12C illustrate how the target 41B is moved across the display so as to follow the gazing direction 12. Thus, despite changes in the gazing direction 12, the target 41B is always projected onto the PRL region 34.

In Training mode, a desired target 46 is always projected onto the PRL area of the retina despite changes in the gazing direction 12, see for example FIGS. 16A, 16B and 16C.

In Daily Use mode, a somewhat different method of operation is required, as detailed with reference to FIGS. 27, 28 and 29.

It will be recognized that the foregoing is but one example of an apparatus and method within the scope of the present invention and that various modifications will occur to those skilled in the art upon reading the disclosure set forth hereinbefore, together with the corresponding drawings.

The invention claimed is:

1. A system for improving a patient's vision, comprising:
   a. means for diagnosing and monitoring a deterioration in macular vision or macular vision loss in a patient's eye, comprising means for testing and mapping a retina by scanning the retina, and
   b. means for augmenting the use of a preferred retinal location (PRL) and eccentric fixation in case the deterioration in macular vision or macular vision loss was detected;
   wherein the diagnosing and monitoring means, and the augmenting means, further including means for applying a focalized stimulus to one location on the retina at a time;
   and wherein the applying means further including eye tracker means for measuring a gazing direction of the patient's eye and means for changing the location of the focalized stimulus accordingly, so as to keep the stimulus on the same location on the retina.

2. The system for improving a patient's vision according to claim 1, wherein the system has several modes of operation including Mapping, Training, and Supervisor/Monitor, and further including means for selecting one of the modes of operation for use as desired.

3. The system for improving a patient's vision according to claim 2, further including means for defining and registering a most suitable retinal locations for PRL, based on the results of the diagnosing and monitoring a deterioration in macular vision or macular vision loss, and wherein the most suitable retinal locations for PRL is defined as the location in the peripheral retina having the least deterioration.

4. The system for improving a patient's vision according to claim 1, further including means for evaluating and registering performance results for each retinal location.

5. The system for improving a patient's vision according to claim 4, wherein the performance results for each retinal location include one or more of the following spatial and temporal parameters: visual acuity, reading acuity, reading speed, contrast sensitivity, crowding, reaction time, saccades, fixation stability, size of healthy area, color test, orientation discrimination and/or optical distortions.

6. The system for improving a patient's vision according to claim 1, wherein the means for augmenting the use of a PRL comprise means for training the patient to constantly focus the visual stimuli with the PRL and to develop a pseudo-fovea.

7. The system for improving a patient's vision according to claim 6, wherein the means for training the patient further include eye tracker means for measuring an eye gazing direction, and means for stabilizing an image on the retina based on results of the gazing direction measurements.

8. The system for improving a patient's vision according to claim 1, wherein the system is implemented as a stationary or portable system, comprising a display or displays, eye tracker means, processor means and control inputs.

9. The system for improving a patient's vision according to claim 8, further including a tri-dimensional (3D) system comprising 3D glasses and a 3D screen, to separate the PRL stimulus to each of the two eyes.

10. The system for improving a patient's vision according to claim 1, wherein the display is part of a personal computer (PC).

11. The system for improving a patient's vision according to claim 1, wherein the system is implemented as a portable system integrated in wearable goggles, and wherein the display or two displays comprise a micro-displays so devised as to present an image on the retina when the micro-display is located close to the eye, and further including a camera or two cameras attached to the goggles.

12. A device for treating patients with a retinal disease, comprising means for mapping multiple parameters of visual performance onto various locations on the retina areas, means for stabilizing an image displayed on each location using eye tracker means, and means for training the patient to constantly focus the visual stimuli with a most suitable retinal location (PRL) and to develop a pseudo-fovea.

13. The device for treating patients with a retinal disease according to claim 12, further including means for reducing visual crowding and visual noise from the visual stimuli, means for monitoring changes of the retinal performance, and means for achieving a rehabilitation function.

14. The device for treating patients with a retinal disease according to claim 12, further including means for moving the image displayed according to the PRL location.

* * * * *